United States Patent
Keller

(10) Patent No.: US 11,058,579 B2
(45) Date of Patent: Jul. 13, 2021

(54) OPHTHALMIC SURGICAL DEVICE FOR ACCESSING TISSUE AND FOR PERFORMING A CAPSULOTOMY

(71) Applicant: Centricity Vision, Inc., Fremont, CA (US)

(72) Inventor: Christopher Guild Keller, El Cerrito, CA (US)

(73) Assignee: CENTRICITY VISION, INC., Fremont, CA (US)

( * ) Notice: Subject to any disclaimer, the term of this patent is extended or adjusted under 35 U.S.C. 154(b) by 0 days.

(21) Appl. No.: 15/846,070

(22) Filed: Dec. 18, 2017

(65) Prior Publication Data

US 2018/0125711 A1    May 10, 2018

Related U.S. Application Data

(63) Continuation of application No. 15/257,680, filed on Sep. 6, 2016, now Pat. No. 9,861,523, which is a
(Continued)

(51) Int. Cl.
*A61F 9/007* (2006.01)
*A61B 18/08* (2006.01)
(Continued)

(52) U.S. Cl.
CPC .......... *A61F 9/00754* (2013.01); *A61B 17/32* (2013.01); *A61B 18/08* (2013.01); *A61B 2018/00291* (2013.01)

(58) Field of Classification Search
CPC .............. A61F 9/00736; A61F 9/00763; A61F 9/00754; A61F 2009/00887; A61F 2009/00889; A61B 2018/00291
See application file for complete search history.

(56) References Cited

U.S. PATENT DOCUMENTS 4,535,771 A    8/1985  Takayama
4,834,094 A    5/1989  Patton et al.
(Continued)

FOREIGN PATENT DOCUMENTS

JP    2001-511662    8/2001
JP    2005-500893    1/2005
(Continued)

OTHER PUBLICATIONS

Chinese First Office Action, Chinese Application No. 201080068246.2, dated Jun. 27, 2014, 20 pages.
(Continued)

*Primary Examiner* — Melanie R Tyson
*Assistant Examiner* — Chima U Igboko
(74) *Attorney, Agent, or Firm* — Fenwick & West LLP

(57) ABSTRACT

A surgical device and procedure are provided for smoothly and easily accessing tissue to perform microsurgery, including a capsulotomy of a lens capsule of an eye. The device includes a handpiece with a tip for insertion into an incision in the cornea of the eye. A sliding element is disposed within the handpiece and a suction cup is mounted to the sliding element. The sliding element can be translated to move the suction cup into and out of the handpiece. A compression mechanism associated with the suction cup and the handpiece compresses the suction cup for deployment through the tip of the handpiece. The suction cup can expand inside the anterior chamber into a cutting position on the lens capsule. A cutting element mounted to the suction cup is used to cut a portion of the lens capsule and to remove the portion from the eye.

15 Claims, 15 Drawing Sheets

Related U.S. Application Data continuation of application No. 14/736,209, filed on Jun. 10, 2015, now Pat. No. 9,456,923, which is a continuation of application No. 13/702,305, filed as application No. PCT/US2010/037627 on Jun. 7, 2010, now Pat. No. 9,173,771.

(51) Int. Cl.
*A61B 17/32* (2006.01)
*A61B 18/00* (2006.01)

(56) References Cited

U.S. PATENT DOCUMENTS

| | | | |
|---|---|---|---|
| 5,423,330 A | 6/1995 | Lee | |
| 5,441,503 A | 8/1995 | Considine et al. | |
| 5,569,280 A | 10/1996 | Kamerling | |
| 5,728,117 A | 3/1998 | Lash | |
| 5,766,171 A * | 6/1998 | Silvestrini | A61B 18/14 606/49 |
| 5,873,883 A | 2/1999 | Cozean et al. | |
| 5,921,999 A | 7/1999 | Dileo | |
| 5,972,011 A | 10/1999 | Pierce et al. | |
| 6,102,906 A | 8/2000 | Phillips | |
| 6,676,658 B2 | 1/2004 | Burbank et al. | |
| 7,074,227 B2 | 7/2006 | Portney | |
| 8,137,344 B2 | 3/2012 | Jia et al. | |
| 8,157,797 B2 | 4/2012 | Boukhny et al. | |
| 8,162,931 B2 | 4/2012 | Ben-Nun | |
| 8,235,978 B2 | 8/2012 | Ben-Nun | |
| 8,591,577 B2 | 11/2013 | Moradian et al. | |
| 8,657,813 B2 | 2/2014 | Ben-Nun et al. | |
| 8,702,698 B2 | 4/2014 | Keller | |
| 2002/0019627 A1* | 2/2002 | Maguire | A61B 18/1492 606/27 |
| 2004/0010284 A1 | 1/2004 | Maloof et al. | |
| 2004/0092982 A1 | 5/2004 | Sheffer | |
| 2004/0092985 A1 | 5/2004 | Parihar et al. | |
| 2004/0106929 A1 | 6/2004 | Masket | |
| 2004/0260254 A1* | 12/2004 | Neilson | A61F 9/0017 604/297 |
| 2005/0283162 A1 | 12/2005 | Stratas | |
| 2006/0100617 A1 | 5/2006 | Boukhny | |
| 2007/0191862 A1* | 8/2007 | Ellis | A61F 9/00754 606/107 |
| 2007/0287999 A1 | 12/2007 | Malecki et al. | |
| 2008/0300531 A1 | 12/2008 | Gills, Jr. | |
| 2009/0216225 A1 | 8/2009 | Ben-Nun | |
| 2010/0094278 A1 | 4/2010 | Jia et al. | |
| 2010/0145447 A1 | 6/2010 | Jia et al. | |
| 2010/0179544 A1 | 7/2010 | Boukhny et al. | |
| 2011/0071524 A1* | 3/2011 | Keller | A61F 9/00736 606/45 |
| 2011/0118734 A1 | 5/2011 | Auld et al. | |
| 2014/0074088 A1 | 3/2014 | Ben-Nun et al. | |

FOREIGN PATENT DOCUMENTS

| | | |
|---|---|---|
| WO | WO 00/48540 | 8/2000 |
| WO | WO 2009/140414 | 11/2009 |
| WO | WO 2010/044988 | 4/2010 |

OTHER PUBLICATIONS

Chinese Second Office Action, Chinese Application No. 201080068246. 2, dated Jan. 26, 2015, 16 pages.
European Extended Search Report, European Application No. 10852995. 9, dated Mar. 12, 2015, 9 pages.
Japanese Office Action, Japanese Application No. 2013-514140, dated Oct. 7, 2014, 4 pages.
Japanese Office Action, Japanese Application No. 2014-130747, dated May 26, 2015, 9 pages.
PCT International Search Report and Written Opinion of the International Search Authority, PCT/US2010/037627, dated Jul. 27, 2010, 10 pages.
Japanese Patent Office, Office Action, Japanese Patent Application No. 2013-514140, dated Feb. 25, 2014, seven pages.
United States Office Action, U.S. Appl. No. 13/702,305, dated Dec. 26, 2014, 16 pages.
Japanese Second Office Action, Japanese Application No. 2014-130747, dated Jan. 26, 2016, 6 pages.
European Examination Report, European Application No. 10852995. 9, dated May 11, 2016, 4 pages.
United States Office Action, U.S. Appl. No. 14/736,209, dated Mar. 21, 2016, 11 pages.
United States Office Action, U.S. Appl. No. 15/257,680, dated Apr. 28, 2017, 21 pages.
United States Office Action, U.S. Appl. No. 15/257,680, dated Oct. 27, 2016, 20 pages.

* cited by examiner

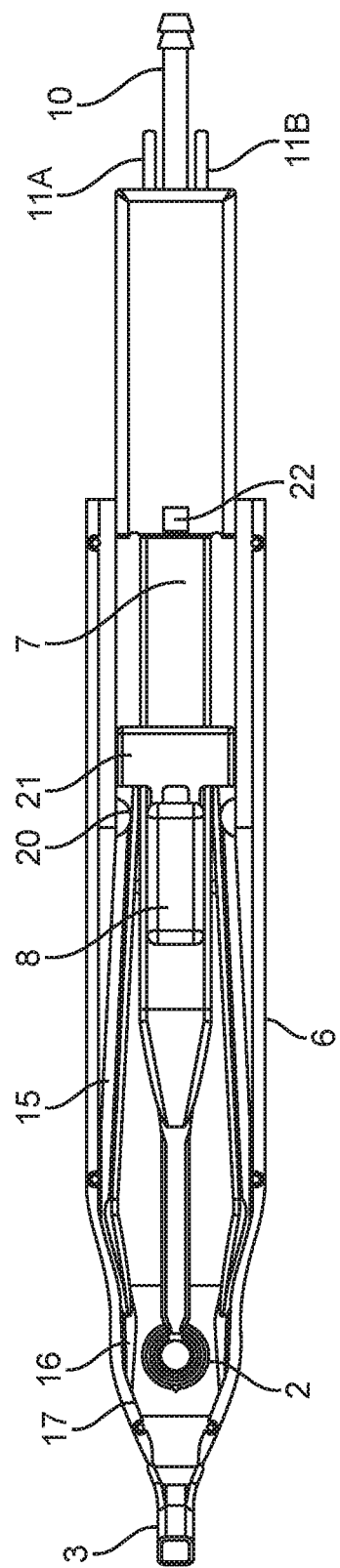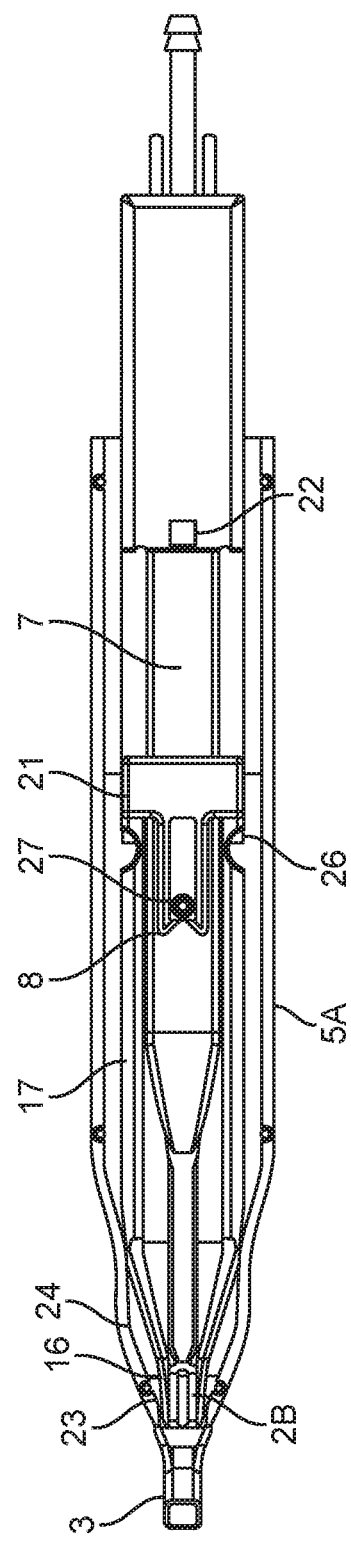

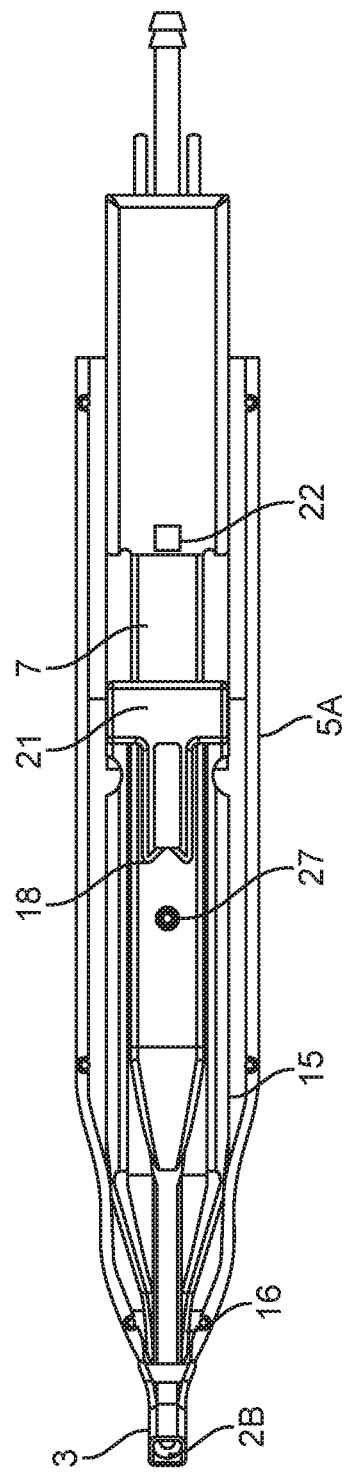
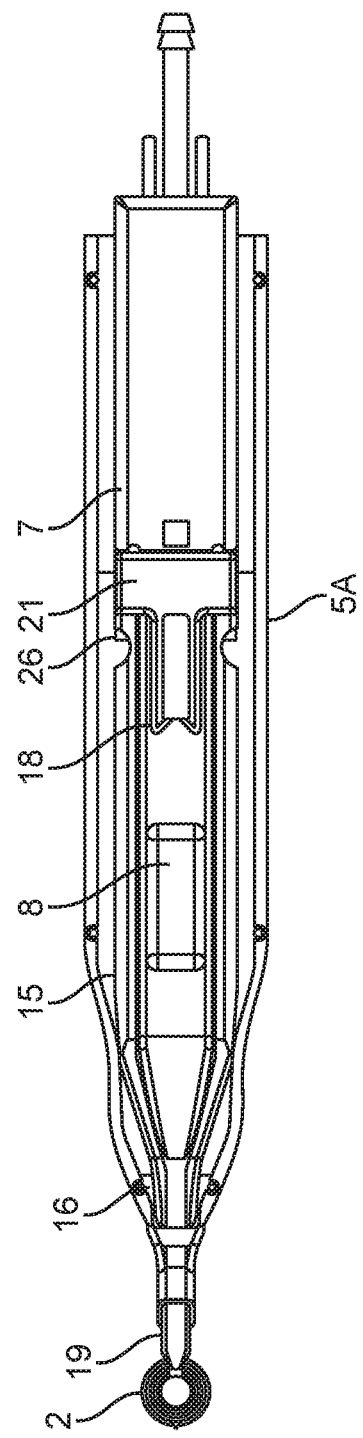
FIG. 7
FIG. 8

OPHTHALMIC SURGICAL DEVICE FOR ACCESSING TISSUE AND FOR PERFORMING A CAPSULOTOMY

CROSS-REFERENCE TO RELATED APPLICATIONS

This application is a continuation of U.S. patent application Ser. No. 15/257,680 filed on Sep. 6, 2016, now U.S. Pat. No. 9,861,523, which is a continuation of U.S. patent application Ser. No. 14/736,209 filed on Jun. 10, 2015, now U.S. Pat. No. 9,456,923, which is a continuation of U.S. patent application Ser. No. 13/702,305 filed on Dec. 6, 2012, now U.S. Pat. No. 9,173,771, which is a national phase application of PCT/US10/37627, filed on Jun. 7, 2010, the entire disclosures of which are hereby incorporated by reference herein, including any appendices or attachments thereof, in their entirety for all purposes.

STATEMENT REGARDING FEDERALLY SPONSORED RESEARCH OR DEVELOPMENT

This invention was made with government support under Grant Number 1R43NS067701-01 awarded by the National Institutes of Health. The government has certain rights in the invention.

BACKGROUND

This invention pertains in general to microsurgery of tissue, and more specifically to procedures and devices for accessing a tissue through another tissue layer, to cut or otherwise manipulate that tissue. For example, the procedures and devices can be used to deliver an ophthalmic surgical device through the cornea to the anterior lens capsule membrane in the anterior chamber of an eye.

Lens cataract is the leading cause of blindness worldwide and surgical treatment by cataract removal is the treatment of choice. A cataract is a clouding that develops in the lens of the eye or in its envelope. The creation of areas of opacity in the lens obstructs the passage of light. The lens of the eye is supposed to be transparent. If the lens develops opaque areas, as in a cataract, the lens must be surgically removed. If no lens is present in the eye, heavy corrective glasses are required to focus an image on the retina. The lens, however, can be replaced with an artificial interocular lens (IOL) to provide better vision after cataract removal. There may also be other reasons to replace a lens that is not serving its functions appropriately.

The removal of the lens for replacement with an IOL is a surgical procedure that requires substantial precision. The lens is completely enclosed by a membrane called the lens capsule, so the surgeon must first cut through the capsule to access the lens. It is important to cut the capsule in just the right way. If the lens capsule has been cut correctly, and not damaged during the cataract removal, then it can be used to hold an IOL. The implantation of an IOL requires the creation of an opening in the lens capsule that is precisely centered, sized, and shaped for implant stability and for optimal IOL function. The matching of the lens capsule opening size to the peripheral margins of the IOL is critical. The goal of the surgeon is to create a perfectly circular (e.g., 5.5+/−0.1 mm diameter) hole in the capsule, centered exactly on the optical axis of the eye, with no tears or defects in the edge of the hole. Tears or defects on the edge of the hole make the capsule very weak and vulnerable to losing the ability to hold the IOL properly. Different IOL designs may require a different diameter for the hole (e.g., ranging from 4.5+/−0.1 mm to 5.75+/−0.1 mm), but whatever the prescribed diameter is, the accuracy of the surgeon in actually achieving it is very important for proper outcome of the cataract surgery. This is especially true of IOLs intended to perform complex optical and focusing functions.

Creating an opening in the lens capsule with this required level of precision is a difficult task for a surgeon controlling and guiding conventional handheld cutting instruments and attempting to trace a precise circular route on the lens capsule. Currently, to perform a capsulotomy (the creation of an opening in the lens capsule), the surgeon typically manually creates a small tear in the anterior region of the lens capsule. With great caution, the surgeon then uses a small needle-like cystotome and/or forceps to try to extend the edge of the tear so as to follow a circular path of the specified diameter and centered on the optic axis of the eye. In practice, it often happens that the hole does not end up circular, or the correct diameter, or centered on the optic axis. There can also be radial tears in the edge of the hole that greatly weaken the capsule. As a result of any of these errors, the capsule may not be able to hold the IOL properly, and optimal visual outcome cannot be achieved.

In addition to the difficulties faced by the surgeon in accessing the lens by performing a precise capsulotomy of the lens capsule, the surgeon must also be able to access the lens capsule itself. The lens is positioned in the anterior chamber of the eye. To access the lens capsule, the surgeon must create an incision in the cornea and carefully insert the capsulotomy instruments through this incision. The same requirement exists in a number of microsurgery procedures in which an incision in a first layer of tissue must be passed through before a second layer of tissue, behind or beneath that first layer, can be accessed. For the surgeon to maneuver the microsurgery instruments through the corneal incision, the incision must be of sufficient size to accommodate these instruments. However, the larger the incision, the greater the risk of infection, of corneal distortion, and of other complications. Microsurgery instruments commonly are not compact enough or are not sufficiently streamlined, making it difficult for the surgeon to minimize the incision size or possibly risking tears or other damage at the incision site. Cutting elements or other sharp components are sometimes exposed during insertion, requiring the surgeon to be very precise and creating further risk of collateral damage to tissue when inserting the instrument through the incision. Further, this insertion often requires multiple steps and sometimes complex maneuvering of instruments by the surgeon, leaving little room for error. Once inserted, instruments are often not easily manipulated and the surgeon may be forced to handle and move multiple separate pieces in a small space. Any of these problems can make it very difficult for a surgeon to access a second layer of tissue behind a first layer, particularly when the second layer is tissue in a very small area, such as within the eye.

Given the drawbacks of existing treatment devices/procedures for accessing tissue, such as the lens capsule, to perform surgery, improved techniques and devices for performing microsurgery are needed.

SUMMARY

Embodiments of the invention include devices and methods for accessing a lens capsule through a cornea of an eye, for performing a capsulotomy in the eye. The lens capsulotomy device includes a handpiece having a tip designed for insertion into an incision in the cornea of the eye. The handpiece has a sliding element disposed therein and a suction cup is mounted to the sliding element for movement into and out of the handpiece. A cutting element is mounted to the suction cup. A compression mechanism associated with the suction cup and the handpiece compresses the suction cup for deployment through the tip. Once the tip of the device is inserted through the corneal incision, the compressed suction cup plus cutting element can be translated in one smooth movement out through the tip of the device and into proximity to the lens capsule. The suction cup plus cutting element expands inside the anterior chamber for creating an opening in the lens capsule.

In operation, the surgeon compresses the suction cup plus cutting element (e.g., by manipulating a knob or other mechanism on the handpiece and the surgeon moves the tip of the capsulotomy device through an incision in the cornea of the eye (though the tip of the capsulotomy device could also be inserted into the incision before compression of the suction cup). The compressed suction cup is deployed out through the tip of the handpiece into the anterior chamber and the suction cup expands inside the anterior chamber into a cutting position on the lens capsule. Suction can be applied to the suction cup for securing the cup to the lens capsule and for pulling the tissue of the lens capsule against the cutting element of the suction cup to cut a portion of the lens capsule (e.g., a circular portion). The suction can then be reduced for releasing the suction cup from the lens capsule while still retaining the excised piece of tissue with the suction cup during device removal. The device is withdrawn through the incision and removed from the eye. Cataract or other lens surgery can then be performed on the eye (i.e., the lens can then be removed by normal methods of cataract surgery).

Other embodiments include devices and procedures for accessing a second layer of tissue behind a first layer of tissue for performing microsurgery or therapeutic work on the second layer, where the tissue is not limited to lens capsule or eye tissue. The surgical device includes a handpiece having a tip for insertion through an incision in the first layer of tissue and a sliding element disposed within the handpiece. A foldable structure (e.g., a suction cup or other collapsible device) is mounted to the sliding element for movement into and out of the handpiece. Compression arms, for compressing the foldable structure, are positioned at sides of the foldable structure and are associated with the handpiece. A manipulation mechanism manipulates the compression arms to compress the foldable structure for deployment out through the tip of the handpiece past the first layer of tissue. Once deployed, the foldable structure expands into an operational position on the second layer of tissue. An operational element associated with the foldable structure is used to engage in microsurgery or therapeutic work on the second layer of tissue. In some embodiments, the operational element is a cutting element used to cut a portion of the second layer of tissue.

In operation, the surgeon applies pressure to sides of a foldable structure inside the handpiece of the device (e.g., by pressing a knob or other handpiece mechanism) to compress the foldable structure. The surgeon accesses a second layer of tissue behind a first layer of tissue by moving the tip of the microsurgical device through an incision in the first layer of tissue (though the tip of the device could also be inserted into the incision before compression of the foldable structure). The procedure further includes translating the sliding element within the handpiece toward the tip to deploy the compressed foldable structure out through the tip of the handpiece past the first layer of tissue. Once deployed, the foldable structure expands into an operational configuration on the second layer of tissue. The surgeon then engages in microsurgery or therapeutic work on the second layer of tissue. In some embodiments, the microsurgery or therapeutic work performed includes cutting of a portion of the second layer of tissue (e.g., with a cutting element associated with the foldable structure).

These techniques enable a surgeon to access and perform minimally invasive microsurgery on tissue, such as the lens capsule. The surgeon can reversibly access the lens capsule via a very small incision, since the foldable structure/suction cup with cutting element, which is larger in diameter (e.g., about 5 mm to 7.5 mm) than the length of the incision (e.g., about 2 mm to 3 mm in length), can be compressed within the handpiece to a small size and smoothly deployed through the tip of the handpiece. This minimizes infection and corneal distortion risks compared with previous access techniques. The cutting element is protected within the device during insertion of the device into the incision, avoiding collateral tissue damage and damage to the cutting element or whatever element is being deployed using the device. Only one smooth suction cup deployment motion, via the compact and streamlined device, is required to access the lens capsule, reducing the amount of maneuvering required by the surgeon to access the tissue.

BRIEF DESCRIPTION OF THE DRAWINGS

FIG. 5 is an uncovered top view of the microsurgery/capsulotomy device with the suction cup stowed inside, according to an embodiment of the invention.

FIG. 6 is an uncovered top view of the microsurgery/capsulotomy device with the suction cup compressed, according to an embodiment of the invention.

FIG. 7 is an uncovered top view of the microsurgery/capsulotomy device with the suction cup compressed and translated into the tip, according to an embodiment of the invention.

FIG. 8 is an uncovered top view of the microsurgery/capsulotomy device with the suction cup deployed, according to an embodiment of the invention.

The figures depict an embodiment of the present invention for purposes of illustration only. One skilled in the art will readily recognize from the following description that alternative embodiments of the structures and methods illustrated herein may be employed without departing from the principles of the invention described herein.

DETAILED DESCRIPTION

Microsurgery/Capsulotomy Device

Embodiments of the invention are described herein in the context of a lens capsule surgery in which a portion of the anterior surface of a lens capsule is cut. This technique may be used for performing a treatment for cataracts in which all or a portion of a lens located within the lens capsule is removed from the eye. The procedure may also be used to create an access hole in the lens capsule through which to implant an artificial lens (e.g., an intraocular lens, or IOL) within the lens capsule. Though often described herein in terms of performing lens capsule surgery, the devices and procedures are not limited to lens capsule surgery, but can also be useful in other treatments of the eye, such as a corneal surgery, treatments for glaucoma, microfenestration of the optic nerve, surgeries involving decemet's membrane, among others. Furthermore, the devices and procedures may also be useful in the delivery of pharmacologic, biologic, and chemical entities and therapeutics. The devices and procedures can also be used to deliver fluids in addition to suction, and the delivery can be specifically localized (e.g., by the suction cup) limiting exposure only to desired tissues. In addition, the devices and procedures may be useful for industrial applications or performing other medical procedures outside of the eye, such as procedures involving excision of delicate membranes or tissue structures, fenestration of brain dura, and others. The devices and procedures can also be used outside of the body (in vitro), on tissue excised and separate from the body, for industrial applications, etc. In these other types of applications, the procedures and devices function generally in the same manner as described regarding the lens capsule surgery, though the components may be differently arranged, sized, shaped to accommodate different tissue.

Figure 1:
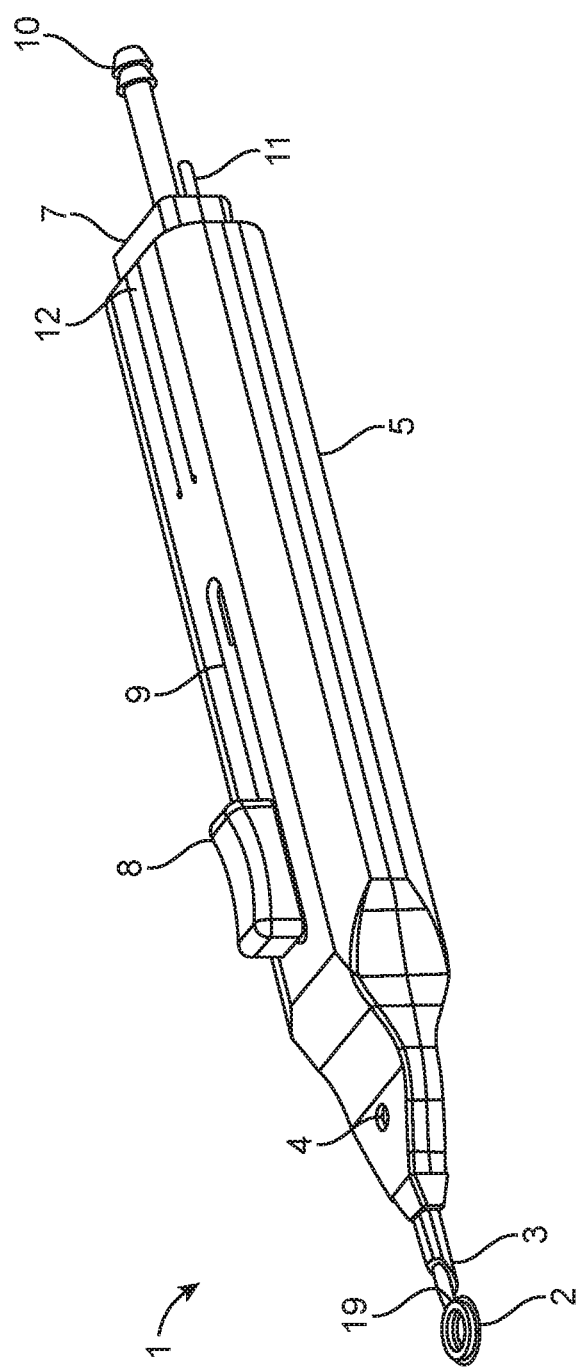
FIG. 1 is a top perspective view of the microsurgery/capsulotomy device with the suction cup deployed, according to an embodiment of the invention.

FIG. 1 is a top perspective view of the microsurgery/capsulotomy device 1 with the suction cup/foldable structure 2 deployed, according to an embodiment of the invention. The device 1 is designed for accessing a second layer of tissue (e.g., lens capsule) behind a first layer of tissue (e.g., cornea) for performing microsurgery. The device 1 includes a handpiece 5 or structure with a housing that can be manipulated by the surgeon for performing the surgical procedure (e.g., to perform the capsulotomy step of lens surgery). The handpiece includes a tip 3 for insertion through an incision in the first layer of tissue (e.g., an incision in the cornea of the eye). The tip 3 is narrow and streamlined in shape so it can easily be slipped into the incision in the tissue without tearing the incision or otherwise damaging the tissue. The tip 3 includes an opening 14 through which the foldable structure or suction cup 2, connected at the end of a stem 19, can be deployed. The handpiece 5 is shown in FIG. 1 as a long, generally cylindrical-shaped structure, though the handpiece 5 can take on a variety of shapes and forms.

The structure deployed through the tip of the handpiece 5 can be a suction cup 2 as show in FIG. 1. However, it can also be any other type of foldable, collapsible, or compressible structure that can be folded. For example, the structure 2 could be another shape required for functioning with a particular tissue type. The device 1 provides a mechanism of delivering a foldable structure of any type or shape through a small opening by allowing for orderly folding of this device. Thus, where "suction cup" is referred throughout this description, it can also be replaced with another type of foldable device. Further, the suction cup 2 shown in FIG. 1 is designed to be folded predominantly along one axis, and specifically it is predominantly compressed laterally, while still remaining flat inside the device 1 (as will be described in more detail below). However, different suction cup or folding structure types may be folded predominantly along a different axis or otherwise compressed for deployment to various tissue types. In some embodiments, the suction cup is folded only along one axis, while in other embodiments the suction cup is folded along more than one axis.

The device 1 further includes a manipulation mechanism that comprises a knob 8 connected via a slot 9 in the housing of the handpiece 5 to a slider/sliding element 7 that can be moved forwards and backwards by the surgeon pushing on the knob 8. A portion of the slider 7 is shown at the end of the handpiece 5 opposite the tip 3. The surgeon can manipulate the knob 8 back and forth along the slot 9. The slot 9 in the housing can restrict the movement of the slider 7 to a maximum forward position and a maximum rear position, as illustrated in FIG. 1. In some embodiments, a storage latch 12 holds the slider 7 in its shipping position prior to use. Manipulation mechanisms other than a knob 8 can also be used to move components within the device, such as a lever, button that is depressed, a switch, a rotatable knob, a flap, and so forth.

In use, the handpiece 5 can be plugged into a hose (e.g., via hose barb 10) that leads to a controlling system that provides air flow and suction. The handpiece 5 can also be plugged into electrical wires (e.g., at electrical connectors 11) that lead to a controlling system that provides electrical current and makes electrical measurements. The device 1 can further include a lumen within the slider 7 to allow fluidic transport from the hose barb 10 to the suction cup 2. The electrical connectors 11 can also connect to the electrical circuit within a lumen of the slider 7. A lubrication hole 4 allows for the application of a suitable lubricant, including viscoelastic (which is normally used inside the eye during cataract surgery) to the suction cup 2 and the passageway through which it will slide. In some embodiments, all or a portion of the device 1 disposable.

Figure 2:
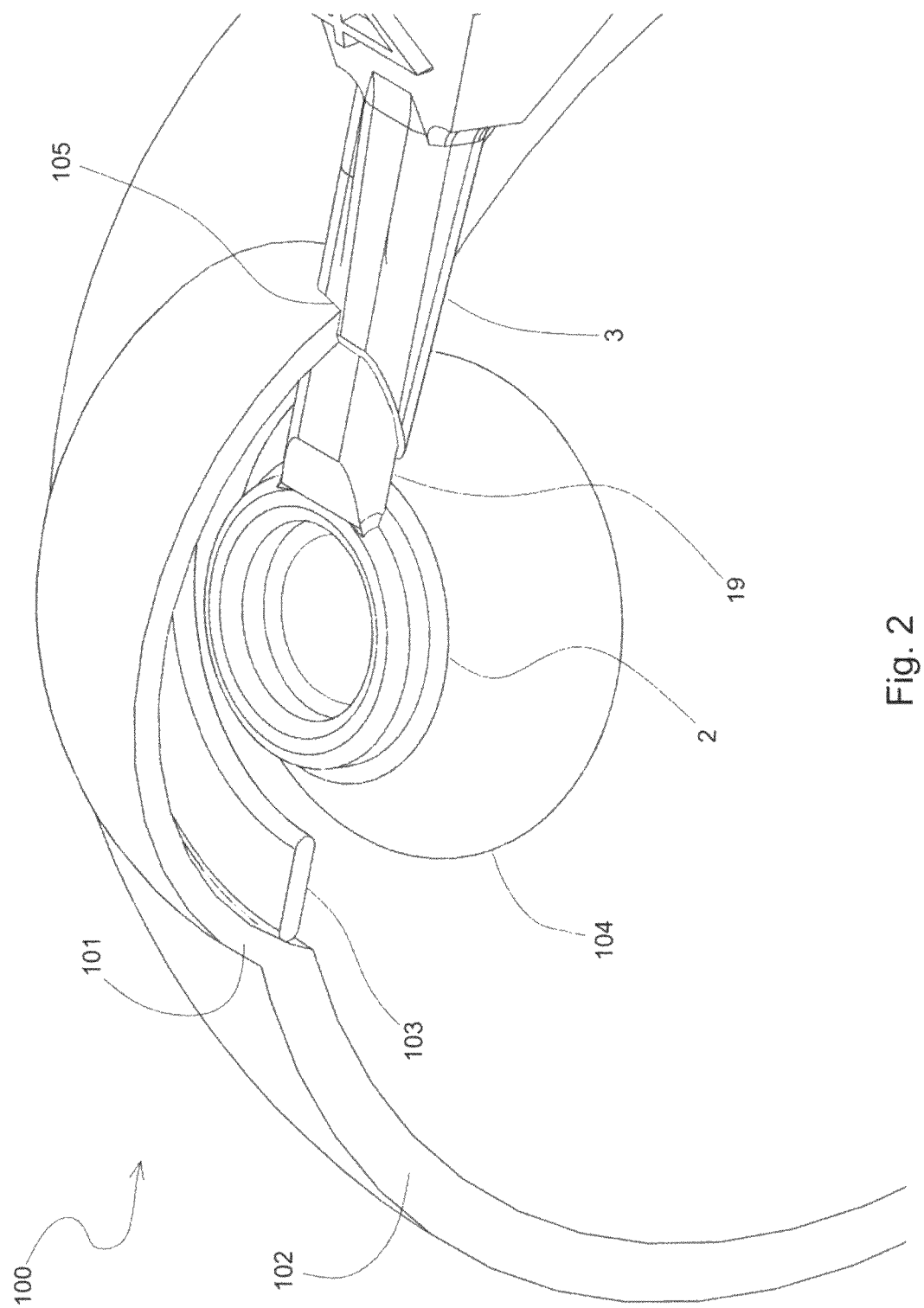
FIG. 2 is a top perspective view of the microsurgery/capsulotomy device in use in the anterior chamber of the eye, according to an embodiment of the invention.

FIG. 2 is a top perspective view of the microsurgery/capsulotomy device 1 in use in the anterior chamber of the eye 100, according to an embodiment of the invention. The parts of the eye 100 illustrated in FIG. 2 include the sclera 102, the cornea 101, the iris 103 and the lens capsule 104. The device 1 illustrated in FIG. 2 is being used by an ophthalmic surgeon to perform a capsulotomy, which is one of the steps that is typically performed in cataract surgery. The capsule 104 is a transparent membrane that encapsulates the lens of the eye 100. In FIG. 2, the surgeon has made an incision 105 through the cornea 101. The insertion tip 3 of the device 1 has a narrowly-shaped leading edge (13, see FIG. 3) to mechanically find the corneal incision 105 and enter it. In FIG. 2, the tip 3 of the device 1 has already been inserted through the incision 105 in the cornea 101, and the suction cup 2 and stem 19 have been pushed through the lumen (14, see FIG. 3) of the insertion tip 3. When the system applies suction via the hose barb 10, the lens capsule is forcibly held against the suction cup 2 and against the cutting element (shown in FIGS. 13, 14, and 18) contained therein.

A circular hole is cut in the anterior capsule 104 so that the lens can be removed, and the IOL can be inserted. In some embodiments, the circular opening in the capsule 104 or other tissue is approximately 5 mm to 7.5 mm in diameter. However, other diameter openings can be created with other embodiments, as desired for various surgical procedures (e.g., 1 mm, 2 mm, 3 mm, 4 mm, 8 mm, 9 mm, 10 mm, 15 mm, 20 mm, and so forth). The circular patch of excised membrane can be held within the suction cup 2 via suction and removed from the eye 100 along with the device 1. Once the device 1 is removed from the eye 100, the excised tissue can be discarded. The rest of the capsular bag can remain undamaged so that it will have the structural integrity needed to hold the IOL.

In some embodiments, the device 1 does not include a cutting element. In these embodiments, the device 1 can include one or more other operational elements for therapeutic work. For example, the device 1 could include a tissue manipulation mechanism for grasping or otherwise manipulating the tissue. As another example, the device 1 could include a mechanism for cauterizing, stretching, adjusting, stabilizing, providing fluids to, or performing other actions on tissue.

Figure 3:
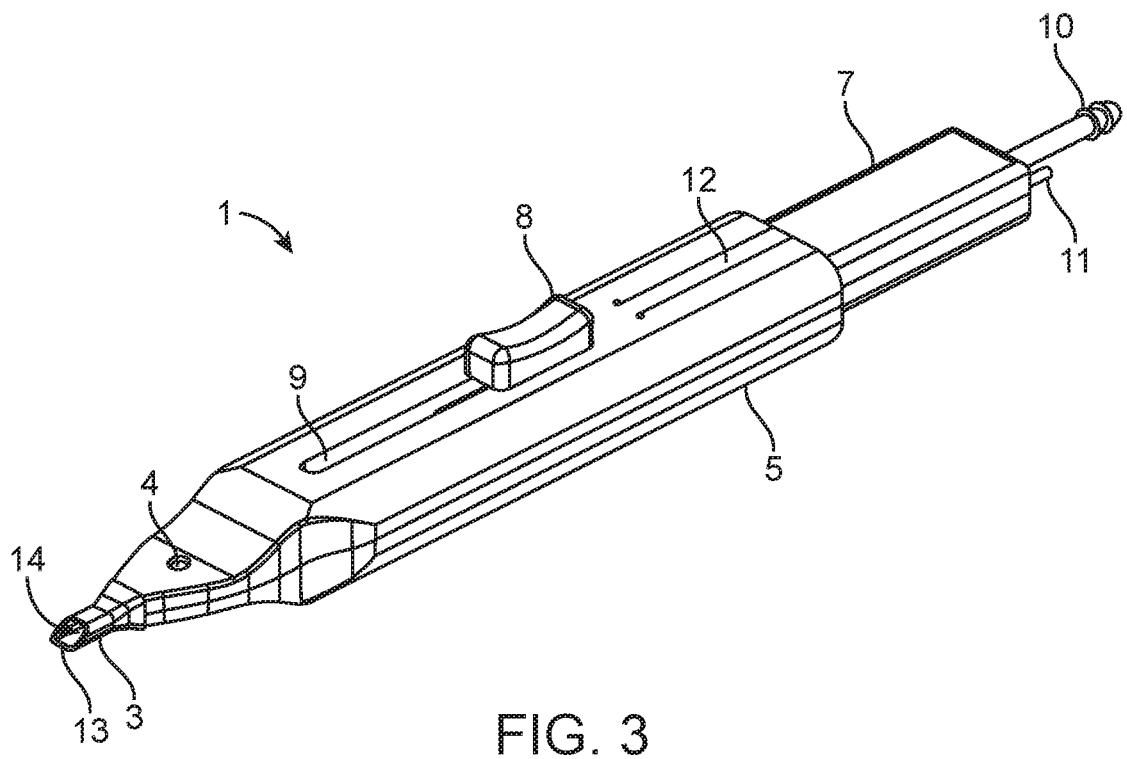
FIG. 3 is a top perspective view of the microsurgery/capsulotomy device with the suction cup stowed inside, according to an embodiment of the invention.

FIG. 3 is a top perspective view of the microsurgery/capsulotomy device 1 in a stowed configuration with the suction cup 2 stowed inside, according to an embodiment of the invention. In some embodiments, the device 1 is shipped to the customer in this retracted configuration to protect the suction cup 2 during shipping. The knob 8 is at the opposite end of slot 9 toward the proximal end of the device 1 (as compared to FIG. 1 which illustrates the knob 8 at the distal end of the slot 9 when the suction cup 2 is extended from the tip 3). The storage latch 12 is engaged with a detent (22, FIG. 5) in the slider 7. The storage latch 12 is designed to prevent unintended movement (e.g., during shipping), but to release under the application of intended force above a predetermined threshold. FIG. 3 also illustrates the leading edge 13 of the insertion tip 3 that is inserted through an incision in the tissue and the lumen 14 of the insertion tip 3 through which the suction cup 2 can pass into and out of the device 1.

Figure 4:
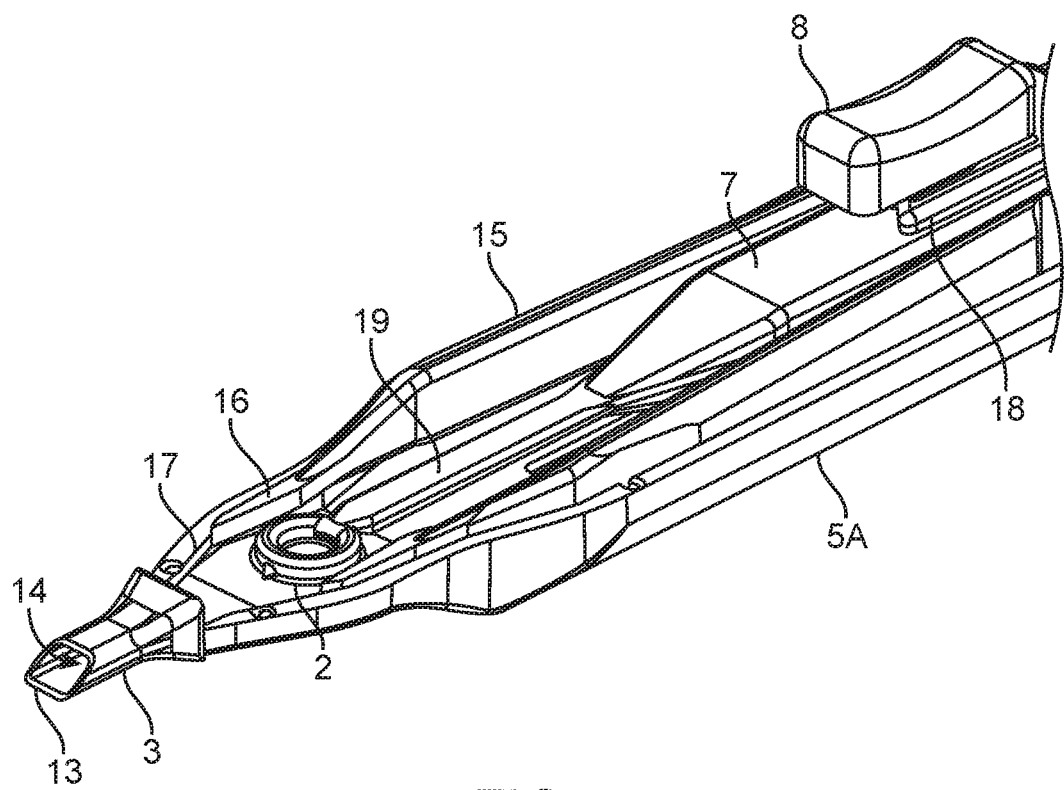
FIG. 4 is an uncovered top perspective view of the microsurgery/capsulotomy device with the suction cup stowed inside, according to an embodiment of the invention.

FIG. 4 is an uncovered top perspective view of the microsurgery/capsulotomy of the housing lower half 5A of handpiece 5 of the device 1 with the suction cup 2 stowed inside, according to an embodiment of the invention. The suction cup 2 is mounted via the stem 19 to the slider 7 within the handpiece 5 for movement into and out of the handpiece 5. The slider 7, which was visible at the proximal end of the handpiece 5 opposite the suction cup 2 in FIGS. 1 and 3, is visible in FIG. 4 within the housing of the handpiece 5. FIG. 4 also shows the knob 8 attached to the slider 7 (which is attached through the slot 9 in the housing of the handpiece 5, as shown in FIGS. 1 and 3). The surgeon can apply force to the knob 8 to slide it distally along the slot 9 to translate the slider 7 distally within the handpiece 5. This slides the suction cup 2 out through the tip 3 for positioning against the second layer of tissue within the first layer (e.g., against the lens capsule within the anterior chamber).

FIG. 4 also illustrates a portion of the compression mechanism associated with the suction cup 2 and the handpiece 5. In the design of device 1, the mechanism includes two compression arms 15 mounted to an arm base 21 (shown in FIG. 5) that is designed to translate relative to the handpiece 5 and the slider 7. The compression mechanism also includes latching arms 18 (shown more clearly in FIG. 6) that surround the location at which the knob 8 attaches to the slider 7. The compression mechanism is used to compress the suction cup 2 to a smaller cross section between the tips 16 of the compression arms 15, so that the suction cup 2 can be deployed through the tip 3 of the handpiece 5 once the tip 3 is inserted into the incision in the tissue. Since the suction cup 2 is compressed, it can easily fit through the tip without tearing or otherwise causing damage to the incision. The tips 16 of the compression arms 15 are moved toward each other to compress the suction cup 2 when they are translated distally within the device 1 and against the closing ramps 17 on the inside of the housing sidewalls.

FIG. 5 is an uncovered top view of the entire microsurgery/capsulotomy device 1 with the suction cup 2 stowed inside, according to an embodiment of the invention. The compression mechanism, which is made up of the arm base 21, compression arms 15, and latching arms 18, is more clearly visible in FIG. 5. In the design of FIG. 5, the arm base 21 is positioned around the slider 7 for translation along the slider 7, though the arm base can be designed in other ways so that it is slidable relative to the slider 7 (e.g., the arm base could be connected to the slider 7, but slidable within a slot in the slider 7, etc.). The compression arms 15 are positioned at the sides of the suction cup 2 and are mounted to the arm base 21. In the stowed position of FIG. 5, the arms 15 are separated and not touching the suction cup 2, and the knob 8 is positioned at a proximal-most position within the latching arms 18 of the compression mechanism. FIG. 5 further illustrates the arm flexure 20 at which the arms 15 bend to bring the arm tips 16 together to compress the suction cup 2. FIG. 5 also shows the detent 22 in the slider 7 with which the storage latch 12 is engaged in the stowed position for safe shipping of the device 1. Both electrical connectors 11A and 11B are visible in FIG. 5 for providing the electrical current to the cutting element of the suction cup 2 (where the cutting element is an electrical element).

FIG. 6 is an uncovered top view of the microsurgery/capsulotomy device 1 with the suction cup compressed 2B, according to an embodiment of the invention. When an outside force is applied to move the knob 8, it slides along the slot 9 on the outside of the handpiece 5 and within latching arms 18 on the inside. FIG. 6 illustrates the latch boss 27, which is the mounting socket via which the knob 8 attaches to the slider 7. The protruding latch bosses 27 on both the top and bottom surfaces of the slider 7 (shown only on the top surface in FIG. slide within the latching arms 18 from a position at the proximal end of the latching arms 18 (close to the arm base 21) to the distal end of the latching arms 18 (toward the insertion tip 3). This translation of the knob 8 (which moves the latch boss 27 within the latching arms 18) moves both the slider 7 (including the suction cup 2) and the compression mechanism distally. The arms 15 slide distally within the handpiece 5 until the tips 16 of the arms 15 contact the beginning 24 of the closing ramp 17. The ramp 17 presses the tips 16 of the arms 15 inward toward each other to compress the suction cup 2. As the arms 15 continue to move distally, the tips 16 slide along the ramp 17 and are further pressed inward until they reach the end 23 of the closing ramp 17 where the suction cup 2 is fully compressed. The arm base 21 contacts one or more arm stops 26 (e.g., molded into the top and bottom housing of the handpiece 5), which prevent the compression mechanism from moving any further within the device 1.

As the suction cup 2 and arm tips advance together, the converging surfaces of the ramps 17 force the arms 15 towards each other (e.g., like a tweezer) by a predetermined amount such that the suction cup 2 is compressed to the desired width. Thus, there is no, or limited, frictional drag on the elastomeric suction cup 2. If the suction cup 2 were to slide directly against the converging sidewalls, the friction could deform it rearwards and prevent the proper lateral compression. The use of intervening rigid tweezer-type tips 16 between the converging sidewalls and the suction cup 2 enables pure lateral compression.

FIG. 7 is an uncovered top view of the microsurgery/capsulotomy device 1 with the suction cup compressed 2B and translated into the tip 3, according to an embodiment of the invention. FIG. 7 illustrates the device 1 after the arm latches 18 have been forced to deflect and release their grip on the latch bosses 27. At this point, the knob 8 can still be slid further along the slot 9 to translate the slider 7 further distally, though the compression mechanism cannot move further distally due to the arm base 21 having contacted the arm stops 26. The latching arms 18 include an opening at the distal end through which the latch boss 27 (connected to the knob 8, not shown here) can move once the arms 15 have reached the end of their translation range. The latch boss 27 can move through the opening to continue translation of the slider 7 as the suction cup 2 is deployed into the tip 3. It is at this point, after suction cup 2 compression and movement to the tip 3, that the surgeon would typically insert the tip 3 through the corneal incision.

FIG. 8 is an uncovered top view of the microsurgery/capsulotomy device 1 with the suction cup 2 deployed, according to an embodiment of the invention. In this Figure, the elastomeric suction cup 2 has been fully deployed and has expanded back to the prior shape it had when stowed. The slider 7 has been translated distally. The proximal-most end of the slider 7, which is wider than the rest of the slider 7, has contacted the arm base 21. Thus, the suction cup 2 can be translated no further. The knob 8 is also shown fully translated to the distal end of slot 9.

Figure 9:
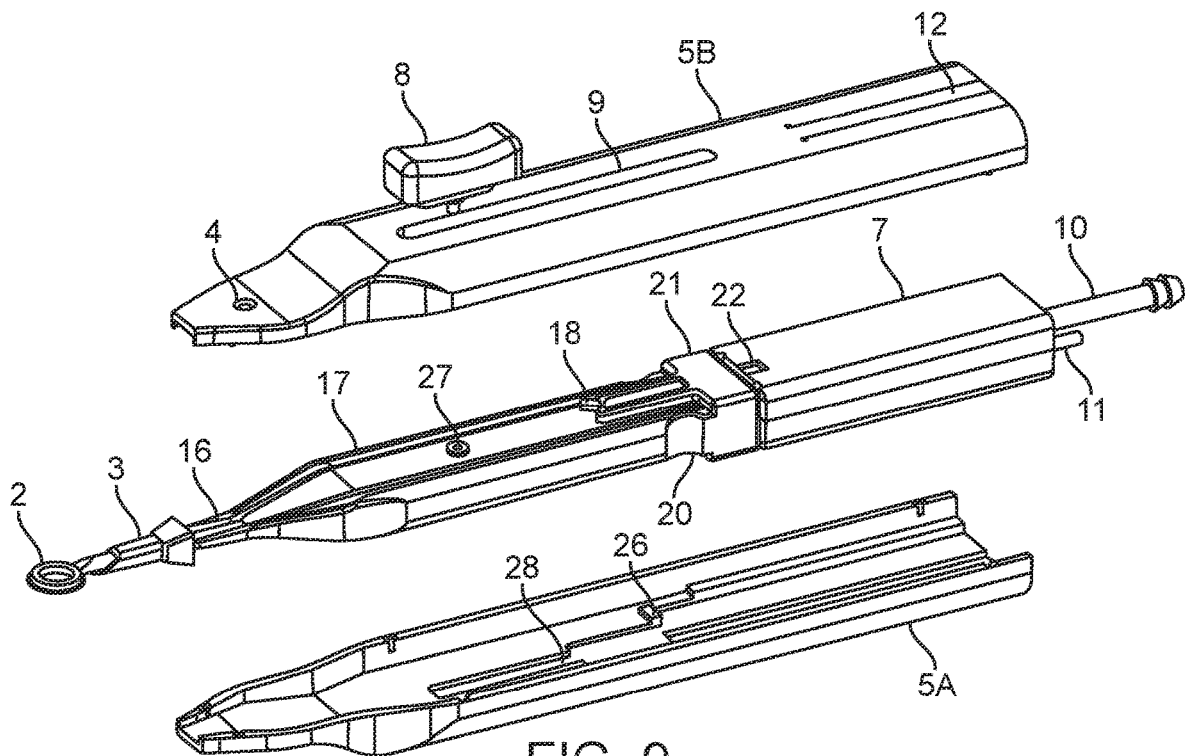
FIG. 9 is a partially exploded perspective view of the microsurgery/capsulotomy device with the suction cup deployed, according to an embodiment of the invention.

FIG. 9 is a partially exploded perspective view of the microsurgery/capsulotomy device 1 with the suction cup 2 deployed, according to an embodiment of the invention. This view shows the various components of the device 1 in a deployed state and illustrates both the upper 5B and lower 5A halves of the housing of handpiece 5. The latch boss 27 has been translated distally, out of the latching arms 18 and the knob 8 as been translated to the distal end of the slot 9. The slider 7 has been translated distally until it contacted the arm base 21. The bottom housing 5A with the slider 7 and compression mechanism removed is also visible. Groove 28 in the bottom housing 5A allows passage of the latch boss 27 on that side of the device 1. The arm stops 26 in the bottom housing 5A, which prevent further translation of the arm base 21 once the suction cup 2 is compressed fully, are also visible in FIG. 9. The arm bend locations 20 are further more clearly visible in FIG. 9.

Figure 10:
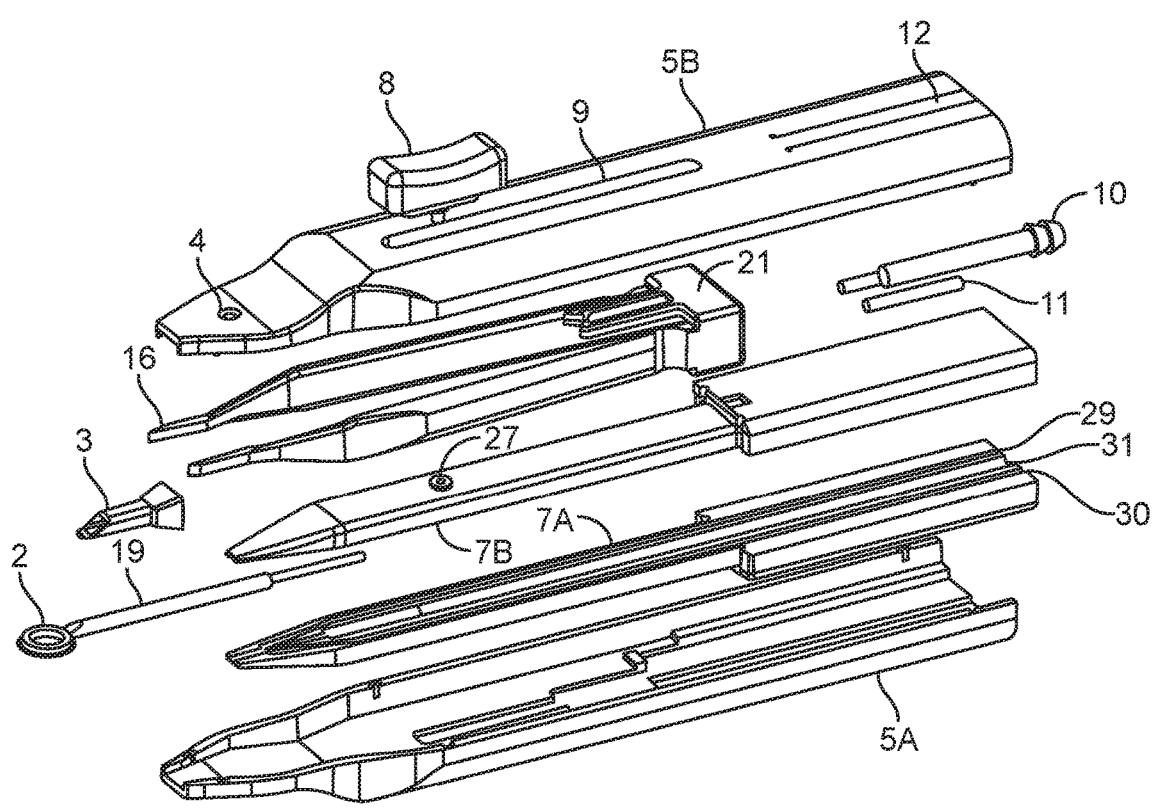
FIG. 10 is an exploded top perspective view of the microsurgery/capsulotomy device with internal components also shown in exploded perspective view, according to an embodiment of the invention.

FIG. 10 is a further exploded top perspective view of the microsurgery/capsulotomy device 1 with internal components also shown separated, according to an embodiment of the invention. In this Figure, the slider 7 and compression mechanism are also separated from each other. In this embodiment, the slider 7 has a bottom half 7A and a top half 7B with fluidic suction lumen 31 and trenches 29, 30 to contain electrical conductors (e.g., wires, not shown). The suction cup 2 plus stem 19 are shown separated from the slider 7 (though the suction cup 2, stem 19, and slider 7 could be a single piece) and the electrical 11 and suction 10 components are shown detached from the device 1. The electrical pins 11 connect to trenches 29, 30 in which electrical wires can be contained. The hose connection 10 connects to the fluidic suction lumen 31 for delivering suction to the suction cup 2.

Figure 11:
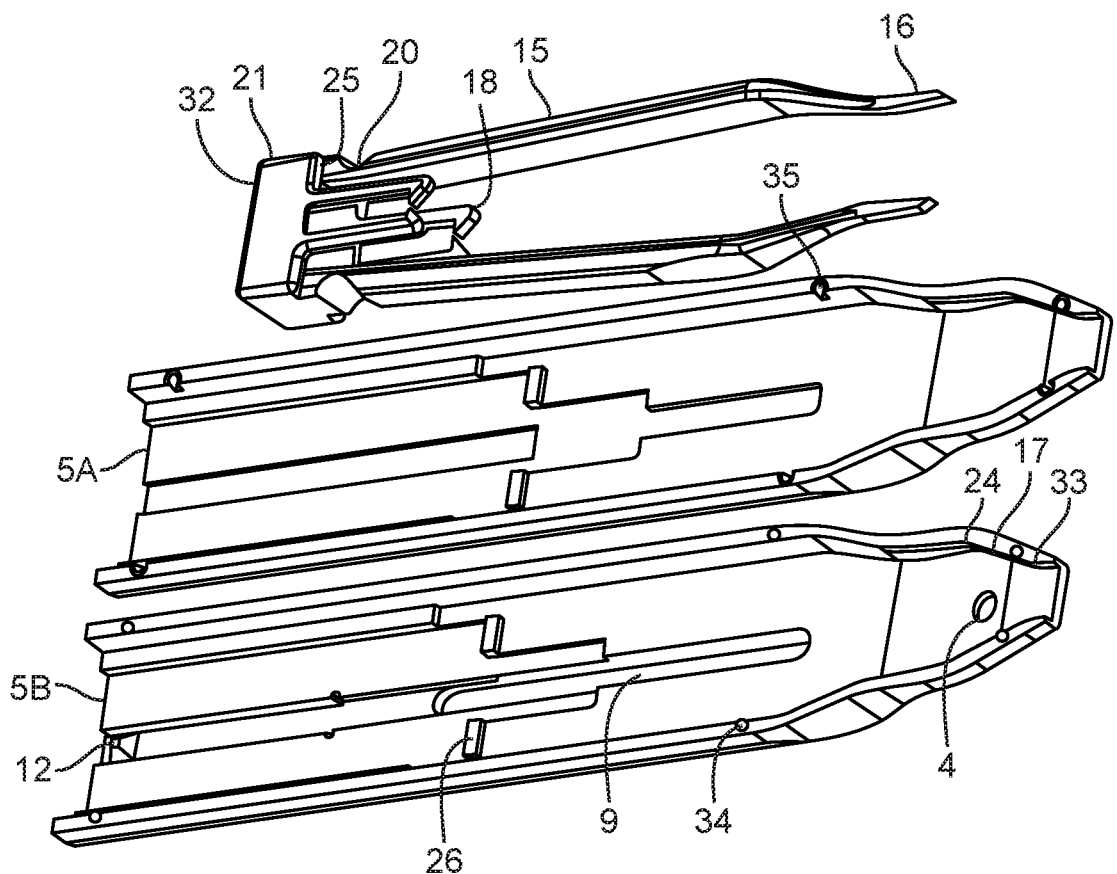
FIG. 11 is an exploded perspective view of the compression arms and part of the handpiece, according to an embodiment of the invention.

FIG. 11 is an exploded perspective view of the compression arms and part of the handpiece, according to an embodiment of the invention. FIG. 11 shows a view of the housing and compression mechanism components to better reveal their features. Pegs 34 in the upper housing 5B engage holes 35 of the lower housing 5A to facilitate assembly. The protruding storage latch feature 12 engages the detent (22, FIG. 12) in the slider 7 when the handpiece 5 is in its shipping configuration. Both the leading 25 and trailing 32 edges of the arm mount 21 are illustrated. A narrowed portion 33 of the housing to which the tip 3 connects is also shown.

Figure 12:
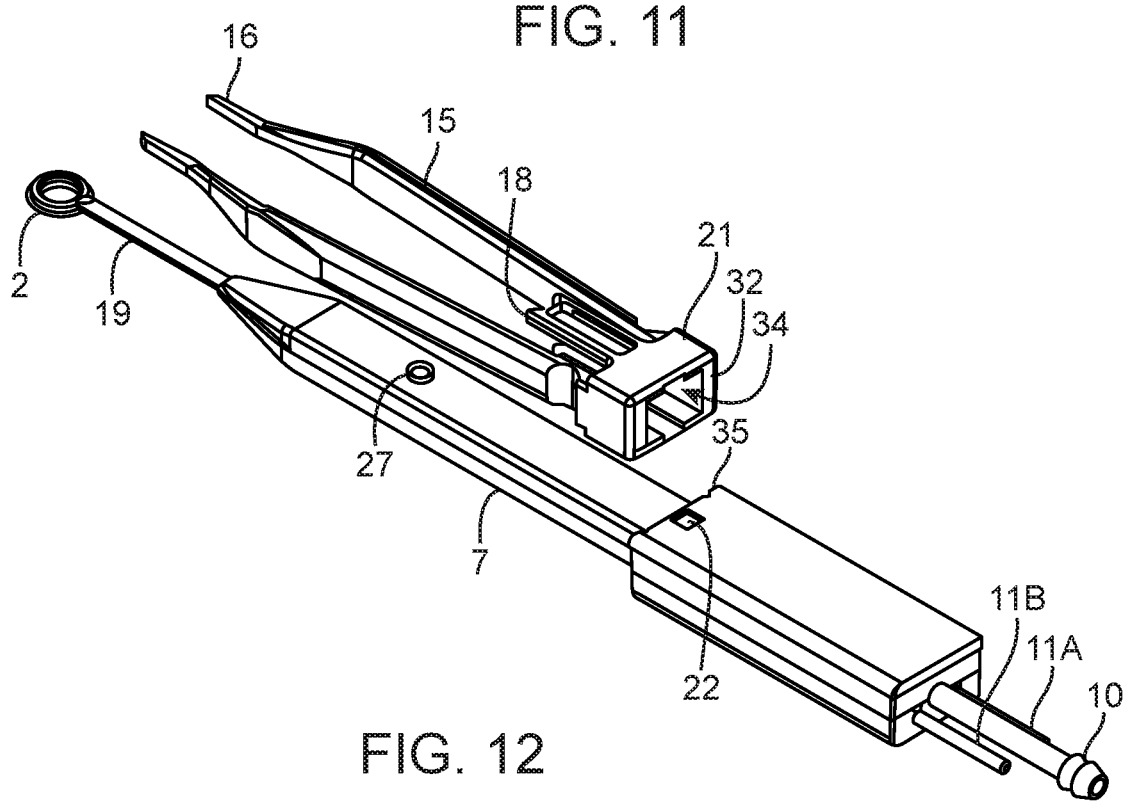
FIG. 12 is an exploded perspective view of the sliding element and compression arms, according to an embodiment of the invention.

FIG. 12 is an exploded perspective view of the slider 7 and compression arms 15, according to an embodiment of the invention. FIG. 12 shows a view of the slider 7 and compression components to reveal how the slider 7 can move through the interior lumen 34 of the arm base 21 until the trailing edge 32 of the arm base contacts the leading edge 35 of the slider base at the fully deployed configuration.

Cutting Element and Suction Cup Designs

Figure 13:
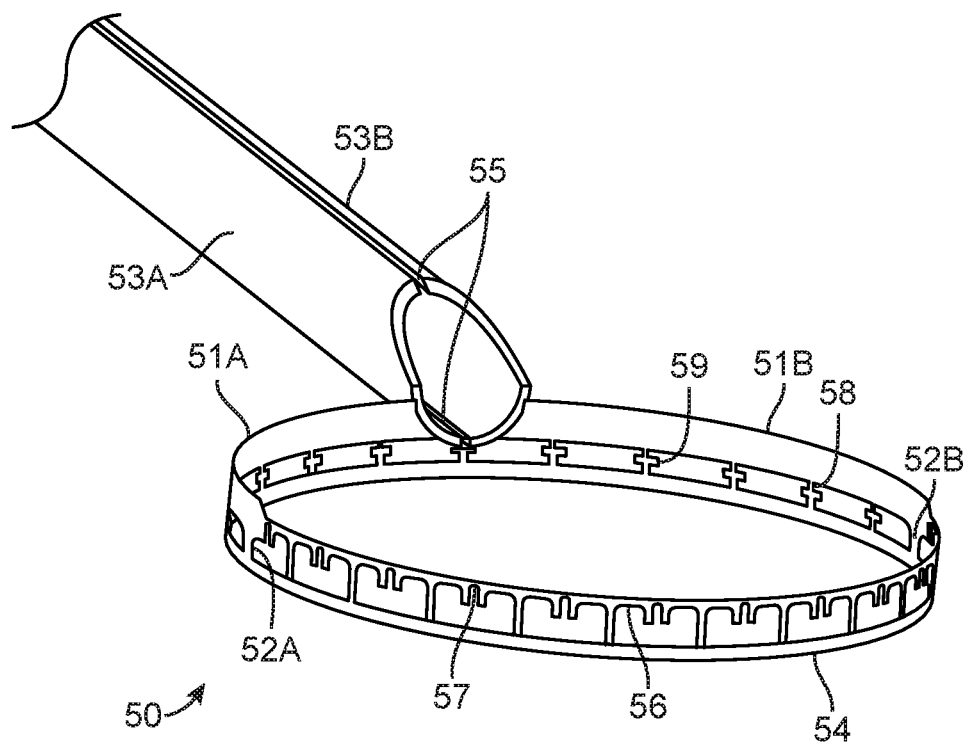
FIG. 13 is a top perspective view of the cutting element, according to an embodiment of the invention.

FIG. 13 is a top perspective view of the cutting element 50, according to an embodiment of the invention. In the embodiment of FIG. 13, the cutting element 50 is an electrode that cuts the capsular membrane, though other designs are also possible (e.g., a sharp knife or multiple sharp knives or teeth). In use, electrical current can flow through rigid lead 53A, through the 90 degree arc lead 51A, through electrode arc lead connection 52A, then into electrode ring 54. Half of the current can flow clockwise and half can flow counter clockwise around the ring 54 to connection 52B and into 90 degree arc lead 51B. Finally, the current flows out through rigid lead 53B. This design beneficially allows the heating of continuous ring 54 to uniformly heat and sever the portion of tissue. Since the current travels through connection 52A to ring 54, and travels both directions along ring 54, the current is distributed evenly on either side of the electrode to heat the tissue more uniformly (as opposed to a ring through which current flows only in one direction from one point in the ring, which will heat the tissue less uniformly). This is just one example of an electrode configuration and current path. Multiple other designs can be used, as well.

The rigid leads 53A, 53B, anchoring tabs 56, 59, and 90 degree arc leads 51A, 51B can be overmolded with elastomer (e.g., silicone, or polyurethane). Gaps 55 that separate the rigid leads 53A, 53B can be filled with the overmolding elastomer and can prevent shorting of current between the rigid leads 53A, 53B. A lumen within the rigid leads can be included for fluid flow and suction, so it typically is not filled with elastomer. Fusible tethers 57, 58 can be designed as very thin ligaments that make the electrode robust for handling so that it retains its shape prior to overmolding. After overmolding, a prescribed sequence of electric currents can be applied to melt the tethers so that they become open circuits. The components of a larger cross section are typically not affected by the currents needed to melt the small cross section tethers 57, 58. This melting process can be performed at the factory prior to shipping. The applied voltages, resulting currents, and resistances (before and after) can be monitored and recorded for quality control to ensure that each unit is properly fabricated. Optionally, the electrode could be made without any tethers.

Figure 14:
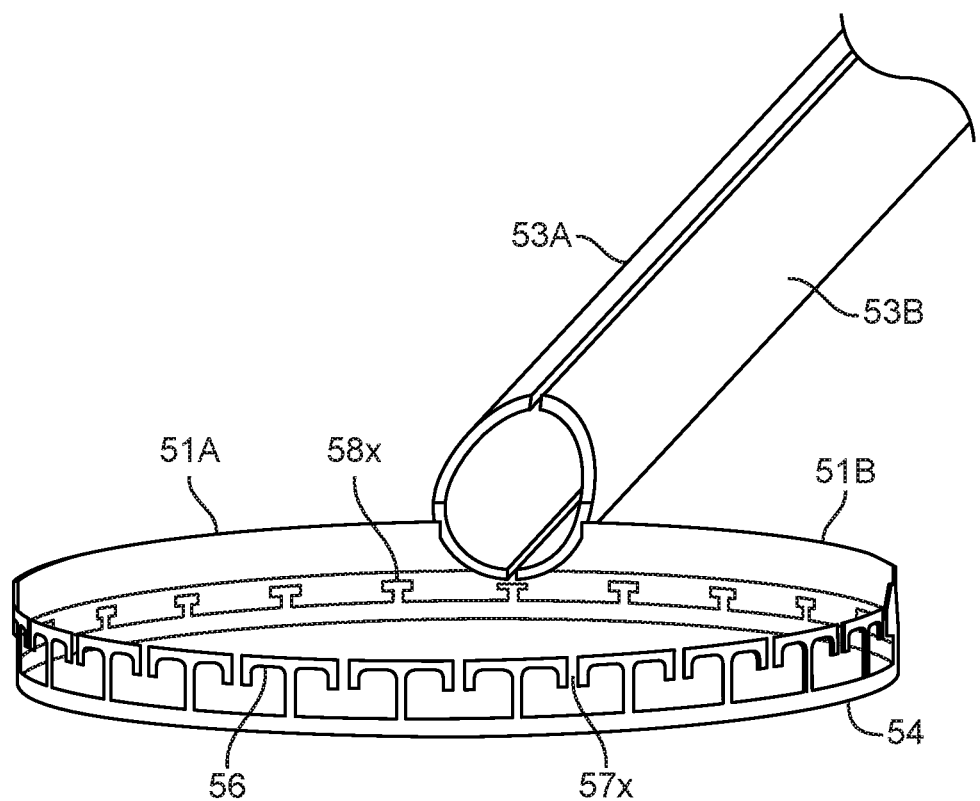
FIG. 14 is a top perspective view of the cutting element with tethers melted (or made without tethers), according to an embodiment of the invention.

FIG. 14 is a top perspective view of the cutting element tethers 57, 58 removed or made without tethers, according to an embodiment of the invention. FIG. 14 shows the electrode with the tethers 57, 58 blown, leaving nonconducting gaps 57x, 58x.

Figure 15:
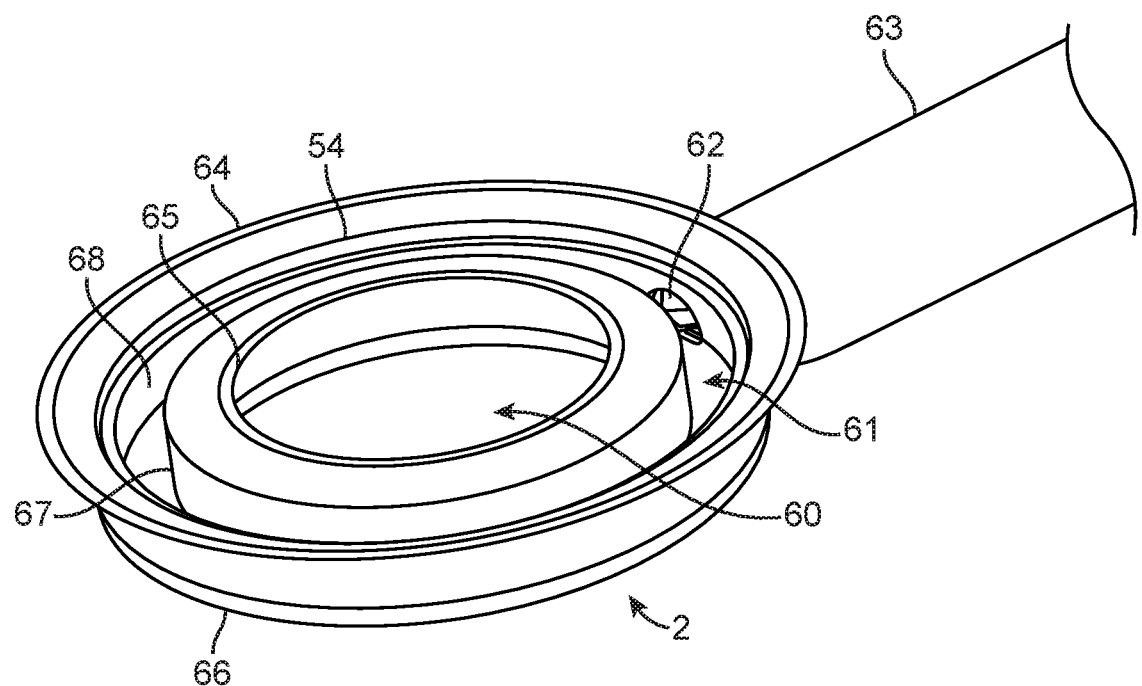
FIG. 15 is a bottom perspective view of the suction cup, according to an embodiment of the invention.

FIG. 15 is a bottom perspective view of the suction cup 2, according to an embodiment of the invention. The suction cup 2 has a roof 66 and an opening 60 in the center. The suction cup 2 also has an interior channel 61 that is bounded on either side by inner diameter (ID) wall 67 and outer diameter (OD) wall 68. The electrode ring 54 is positioned on the other side of OD wall 68.

When the suction cup 2 confronts the lens capsule 104 and suction is applied through lumen 62, the pressure in the channel 61 of the suction cup 2 can decrease. The lumen 62 connects through stem 63, through the device 1, and through hose barb 10 to the suction mechanism for applying suction. The outer diameter (OD) lip 64 and the inner diameter (ID) lip 65 of the suction cup 2 can be pulled against the capsular membrane 104 to form a low leakage seal so that the channel 61 pressure can be decreased further to a predetermined value. The suction can also provide a vacuum seal against the tissue. The suction can further pull portions of the tissue up into the suction cup 2 for securing the suction cup 2 against the tissue or for permitting severing of the tissue using the cutting element. The applied suction force can stretch the capsular membrane over the edge of the cutting element to create a state of high tensile stress exactly on the circle where cutting is desired. Suction can also be used to retain the cut portion of tissue inside the device 1 during removal. Since the cutting element is built-in directly to the device 1 that also provides the suction capabilities, the device 1 can be used in a one-step procedure for performing a capsulotomy.

The OD lip 64 of the suction cup 2 has a flared skirt design extending from the edge around the outer periphery of the suction cup 2. The flared skirt allows the suction cup 2 to rest with low force against the curved surface of the capsule 104 and allows the suction cup 2 to be vacuum sealed against the capsule 104 for the cutting procedure.

Figure 16:
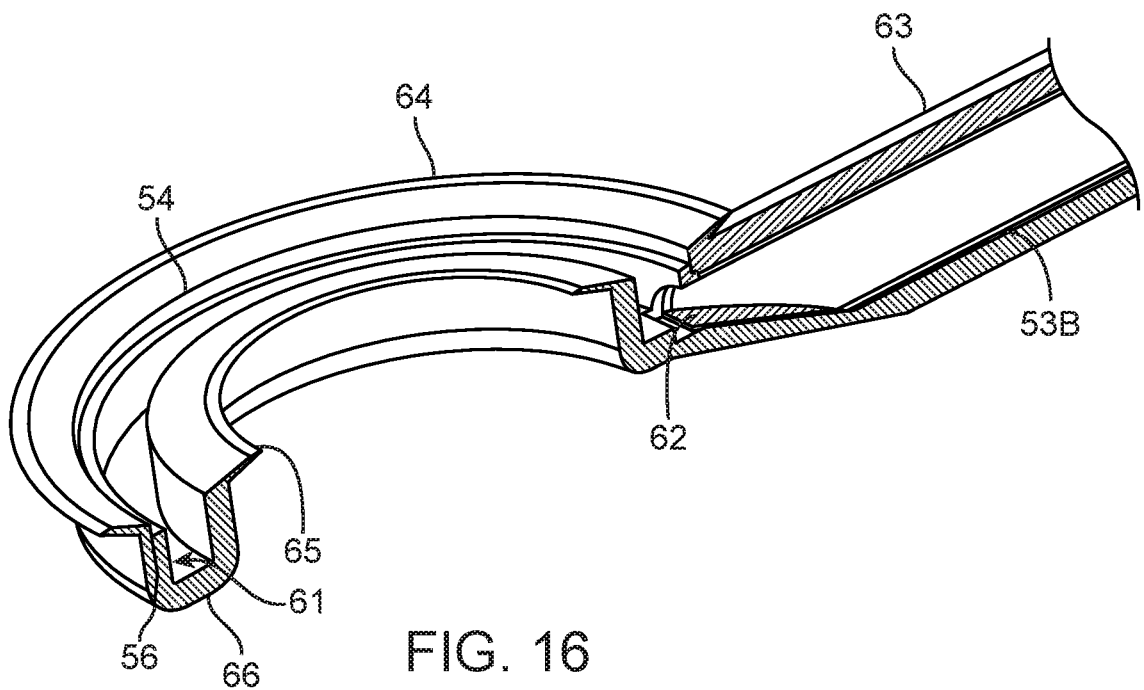
FIG. 16 is a cross-sectional bottom perspective view of the suction cup, according to an embodiment of the invention.

FIG. 16 is a cross-sectional bottom perspective view of the suction cup, according to an embodiment of the invention. The anchoring tabs 56 of the cutting element 50 are embedded in the overmolded elastomer. The rigid lead 53B is shown inside stem 63 of the suction cup 2. The lead 53B is in electrical connection with electrode ring 54. The lumen 62 of the stem 63 is connected to the channel 61 in the suction cup 2 for providing the suction.

Figure 17:
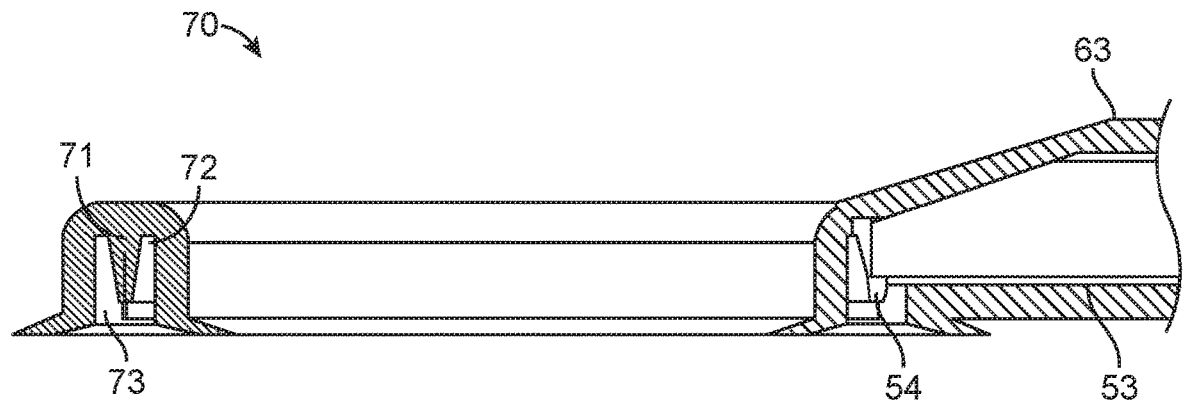
FIG. 17 is a cross-sectional side view of another design of the suction cup, according to an embodiment of the invention.

FIG. 17 is a cross-sectional side view of another design of the suction cup 70 (e.g., midridge or dual channel suction cup design), according to an embodiment of the invention. FIG. 17 shows the exposed electrode ring 54 held by a supporting elastomer ridge 71 located in the middle of the channel 61. This creates two suction channels 73, 72 so the capsular membrane 104 can be stretched forcibly over the edge of electrode 54.

Figure 18:
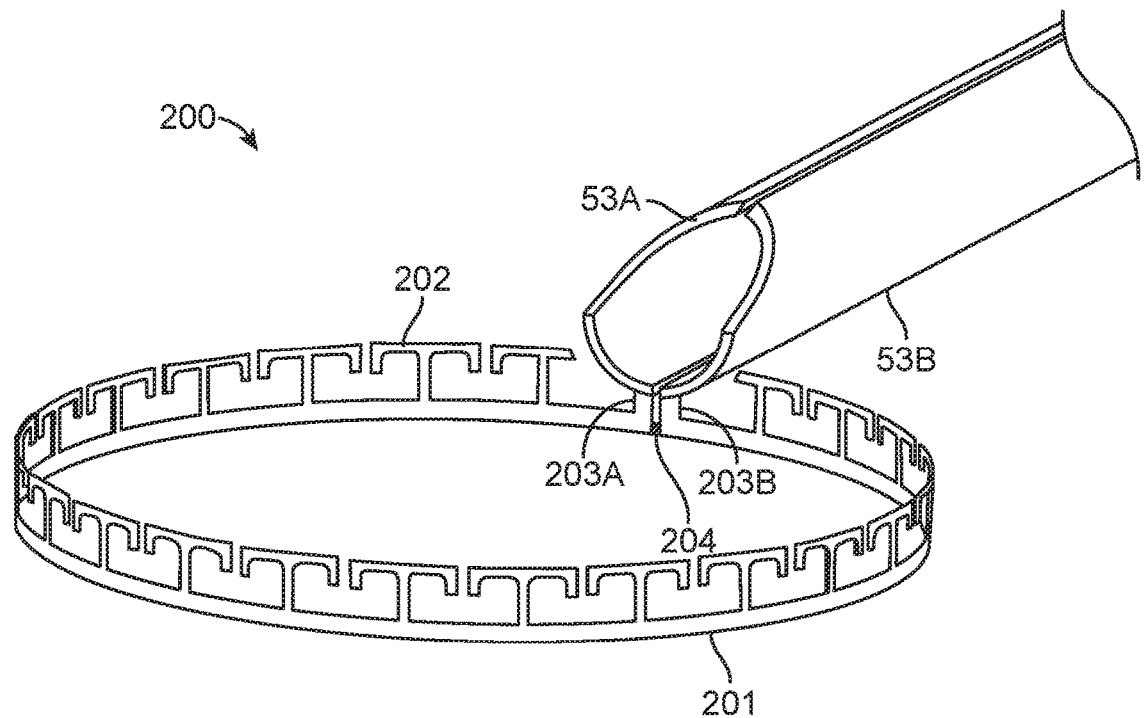
FIG. 18 is a top perspective view of another design of the cutting element, according to an embodiment of the invention.

FIG. 18 is a top perspective view of another design of the cutting element 200, according to an embodiment of the invention. In use, current can flow from rigid lead 53A through connecting lead 203A and into electrode ring 201. A fraction of the current can proceed around ring 201, and the remaining fraction can go through gap material 204, to connecting lead 203B. The fraction that flows through gap 204 can be zero if the material there is not conductive. But if the gap is sufficiently small, the cutting action of the heat from electrical discharge can be designed to bridge the gap so that the entire circle of the capsular membrane patch is cut. If the gap material is conductive, gap 204 can be designed (by having proper length width and thickness) to yield the same power dissipation per millimeter of circumferential length as occurs around ring 201 to achieve uniform heating and cutting action for the full circle. Example constructions can include electroformed nickel or steel for rigid leads 53A and 53B and gap 204. Electrode ring 201 can be electroformed gold or nickel, or etched stainless steel. Anchoring tabs 202 are also shown in FIG. 18, similar to the tabs 56 shown in FIG. 14. In the embodiments of FIGS. 13, 15, and 18, the cutting element is a circular cutting element mounted to the underside of the suction cup. However, the cutting element can take other shapes (e.g., elliptical, square, rectangular, irregular, and other shapes) for different types of surgical procedures where a differently shaped incision in the tissue is desired. Similarly, the suction cup can take on other shapes, as well.

Embodiments of device 1 can be used with electrical, mechanical, and combined electro-mechanical cutting elements, though other designs could be used as well. The electrical cutting element functions as a resistor. A very short electrical pulse quickly heats up the element (e.g., to greater than 500° C., such as 600° C., 700° C., 800° C., 900° C., 1000° C., 1200° C., 1500° C., and so forth). In some embodiments, the heating process lasts for a few microseconds (e.g., 10 microseconds or less), though heating times can differ in other embodiments (e.g., 1 microsecond, 5 microseconds, 10 microseconds, 20 microseconds, 1 millisecond, 5 milliseconds, etc.). The duration of the electrical discharge is too short for heat to travel more than a few microns by conduction from the cutting element, so for a few microseconds the thin layer of water that is trapped between the capsule and the cutting element absorbs the energy of the discharge and forms steam. The steam expands rapidly at high pressure and increases the tensile stress in the capsule enough to tear it. Since the electrical current is applied for only a few microseconds, tissue is not burned as it is with electrocautery instruments, and so the device 1 avoids the risks associated with burning tissue in a patient's eye, with possible collateral damage to nearby tissue, with lengthy application of heat, and other problems. In addition, the electrical cutting element of device 1 completes the severing of the tissue to free the severed piece from the capsule 104, unlike electrocautery devices that often require tweezers to remove the severed piece. Further, in some embodiments, the cutting element has a mass of 0.35 milligrams or less, so bulky heating elements are not required as are commonly found with electrocautery instruments.

Where the cutting element is mechanical, the element has one or more ultrasharp microteeth (or other tissue-severing knife or mechanism) that pierce the capsule as the force of suction pulls the membrane past the teeth to sever the circular patch. Mechanical knife devices used in the past for performing capsulotomies use the knife to stretch the tissue to provide enough force against the cutting edge. In contrast, in this device, the reaction force needed for cutting with the mechanical cutting element of device 1 comes from suction supplied by the device. The suction pulls the tissue perpendicularly onto the cutting edge, so there is no lateral distortion away from where the cut is supposed to go, and precision microcuts can be reproducibly made. In addition, a complete cut can be made with the cutting element, as opposed to the multiple passes that are frequently required with microknives used in the past. The cutting element can be a continuous ring similar to those shown in FIGS. 13, 14, and 18, or can be a non-continuous ring.

Where the cutting element is a combined electro-mechanical cutting element, it has one microtooth (or optionally, more than one) or other tissue severing mechanism that produces an initial tear in the capsule. The tear is propagated using the electrical cutting element design for applying a short electrical pulse, as explained above. The tear can be propagated to complete the capsulotomy by a lower steam pressure than would be required for an intact capsule.

Figure 19:
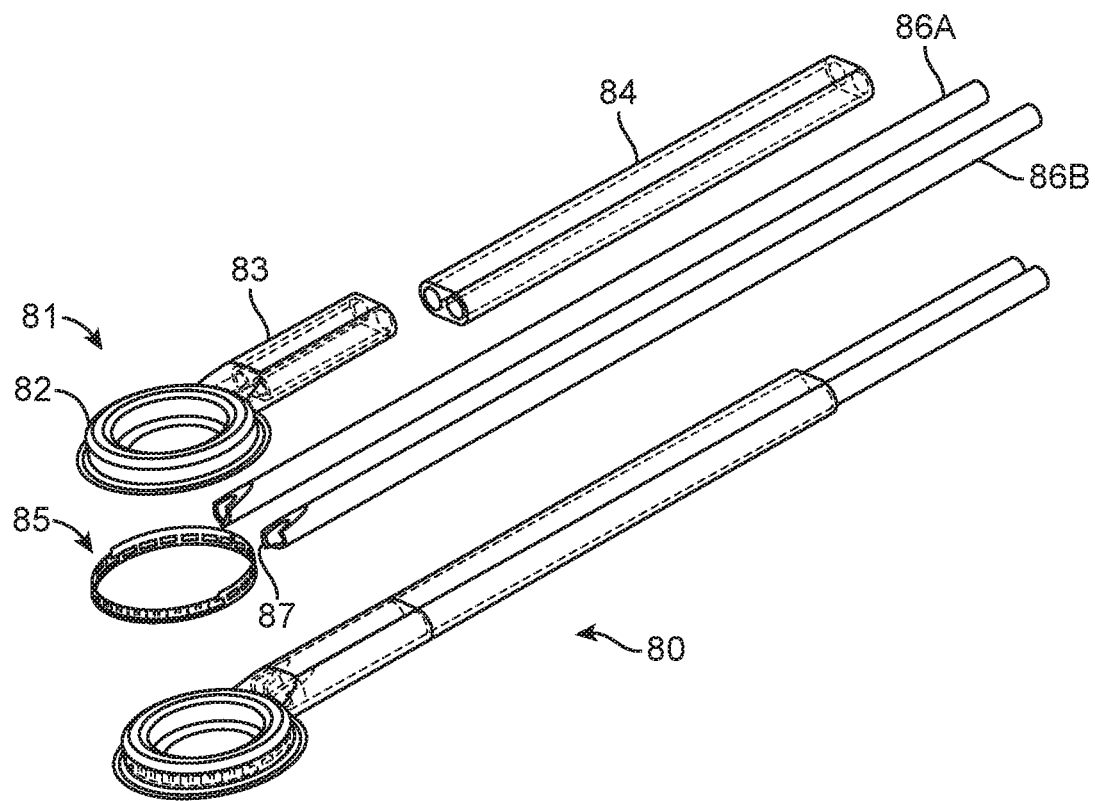
FIG. 19 is an exploded top perspective view of another design of suction cup and the cutting element involving dual tubing, according to an embodiment of the invention.

FIG. 19 is an exploded top perspective view of another design 80 of the suction cup and the cutting element involving dual tubing, according to an embodiment of the invention. The design is shown both assembled and disassembled. The FIG. 19 design 80 includes two pieces of tubing 86A, 86B (e.g., stainless steel tubing) that are assembled in rigid polymer stem 84. The shaped ends 87 of tubes 86A, 86B are joined to electrode 85, and overmolded with elastomer 81 to form suction cup 82 with stem 83 to hold on to the tubing. Other geometries can include two concentric conducting tubes separated by an insulating layer, one tube and an adjacent wire insulated from each other, a nonconducting tube with two adjacent wires, and so forth.

Other Microsurgery/Capsulotomy Device Designs

Figure 20:
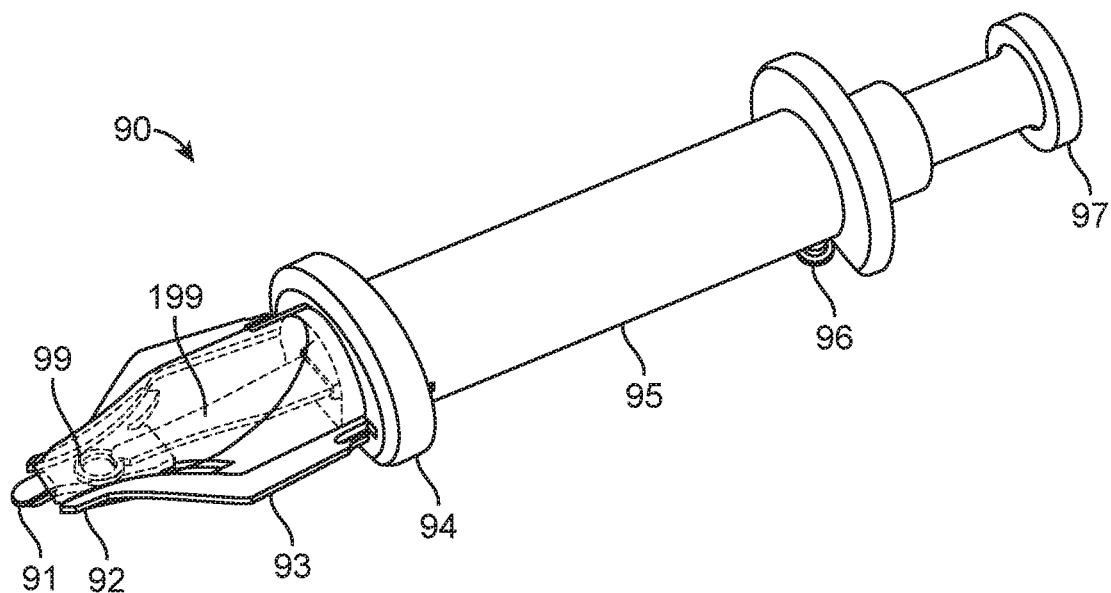
FIG. 20 is a top perspective view of another design of the microsurgery/capsulotomy device with the suction cup stowed, according to an embodiment of the invention.

FIG. 20 is a top perspective view of another design of the microsurgery/capsulotomy device 90 with the suction cup stowed, according to an embodiment of the invention. In FIG. 20, the device 90 is in a stowed (or as-shipped) configuration with the suction cup 99 protected within the device. This design is an external compression mechanism handpiece design 90. The manipulation mechanism includes a piston 97 for translating the suction cup 99 from the device 90 and the compression mechanism includes an external slidable ring/member 94 and the compression arms 93 that are attached to a housing of the handpiece 95. The slidable ring 94 is slidably attached to the handpiece 95 for sliding distally, toward the suction cup 99, and over the compression arms 93 positioned on either side of the suction cup 99, pressing the tips 92 of the arms 93 together to compress the suction cup 99.

The suction cup 99 is further attached to a stem 199 that connects to a sliding element within the device 90, which is connected to the piston 97. The piston 97 is manipulated or pressed distally toward to suction cup 99 to distally push the sliding element inside the device 90. This moves the stem 199 and suction cup 99 distally. The tip of the device 90 includes two insertion fingers 91 (e.g., two lips that can be designed to be compliant) disposed at the tip of the handpiece for maintaining the compressed suction cup in a flattened position as it is translated out of the tip and to the tissue. In the embodiment of FIG. 20, the fingers 91 are sloped inward toward each other at the tip and are pressed together to form a wedge for sliding cleanly through the incision. The fingers 91 are configured to separate with pressure from the suction cup 99 advancement out of the handpiece 95. In the FIG. 20 embodiment, the distal portion of the handpiece 94 is designed to have an upper flat portion and a lower flat portion that also help to hold the suction cup 99 flat during deployment. The compression arms 93 are designed to slide between the upper and lower portions to compress the suction cup 99 laterally. The hose connector 96 for providing suction to the suction cup 99 is just visible in FIG. 20.

Figure 21:
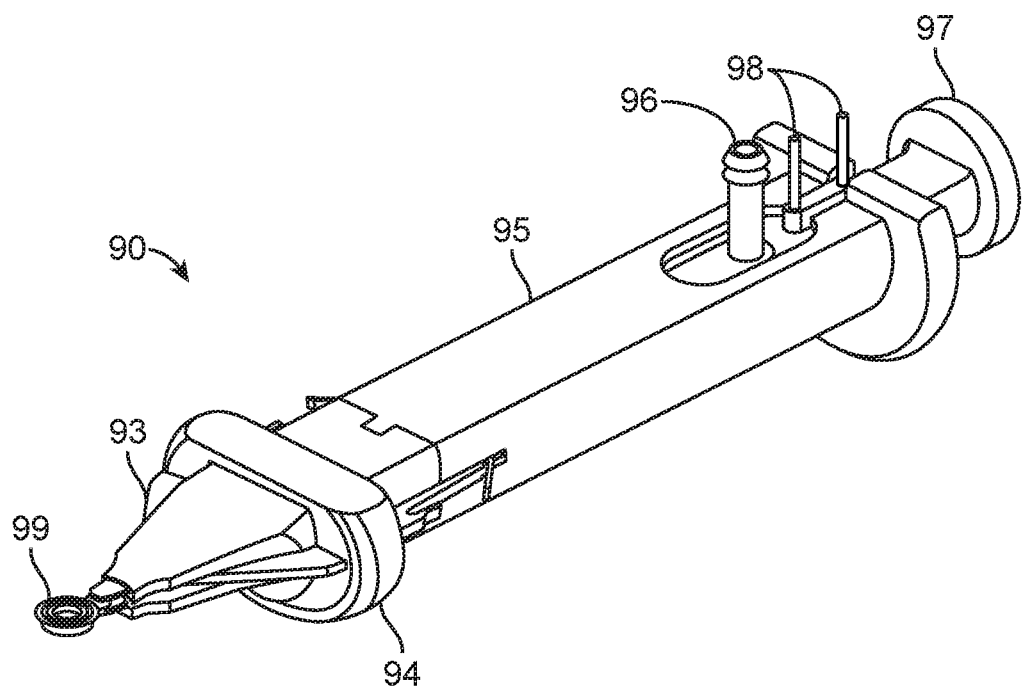
FIG. 21 is a bottom perspective view of another design of the microsurgery/capsulotomy device with the suction cup deployed, according to an embodiment of the invention.

FIG. 21 is a bottom perspective view of the FIG. 20 design of the microsurgery/capsulotomy device 90 with the suction cup 99 deployed, according to an embodiment of the invention. This figure better illustrates the hose connector 96 that provides fluid and/or suction to the suction cup (in a manner similar to that done in device 1) and electrical connectors 98 that provide electrical current into the device and to a cutting element in the suction cup 99. The cutting element in device 90 can be any of the cutting element designs described above. For cutting elements that are not electrical in either devices 1 or 90, the electrical connections and components may not be included in the design.

Figure 22:
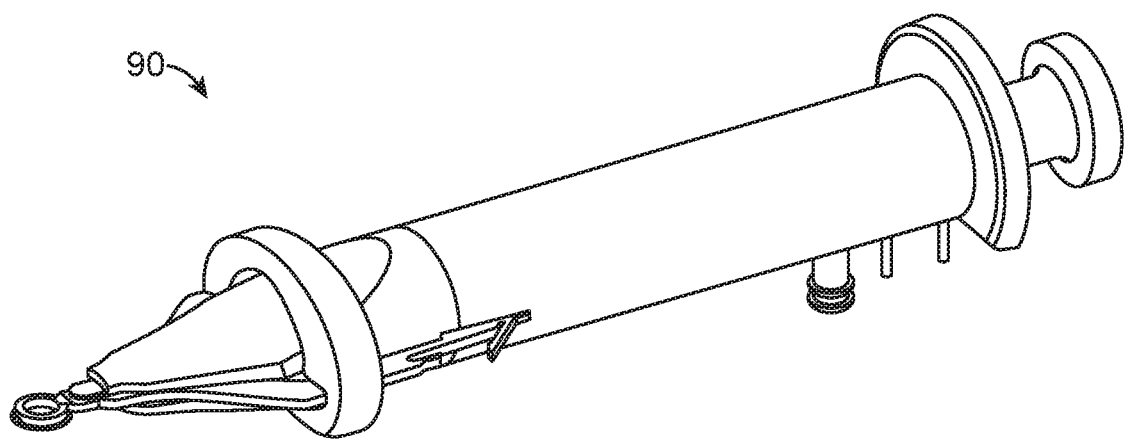
FIG. 22 is a top perspective view of another design of the microsurgery/capsulotomy device with the suction cup deployed, according to an embodiment of the invention.

FIG. 22 is a top perspective view of the FIGS. 20, 21 design of the microsurgery/capsulotomy device 90 with the suction cup 99 deployed, according to an embodiment of the invention. Upon deployment, the suction cup 99 expanded back into its prior shape.

Surgical Procedure

Figure 23:
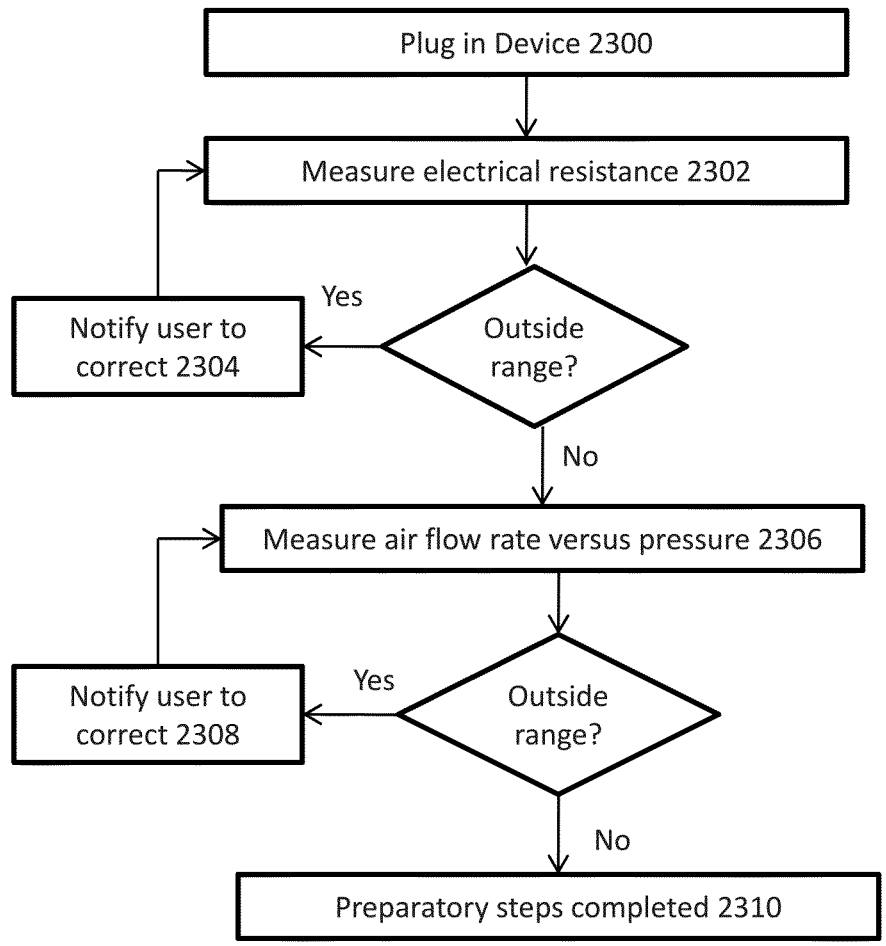
FIG. 23 is a flow chart illustrating preparatory steps for the microsurgery/capsulotomy procedure, according to an embodiment of the invention.

FIG. 23 is a flow chart illustrating various preparatory steps for the microsurgery/capsulotomy procedure, including a procedure that can be used with devices 1, 90, according to an embodiment of the invention. For FIGS. 23-25, the steps can vary across different procedures, including having additional or different steps than those shown, and the steps can occur in different orders.

In FIG. 23, the surgeon/user connects or plugs in 2300 a device into a connector to the nondisposable controlling system. The connector provides for the transmission of suction to the lumen of the device and electrical current to the electrode of the device (i.e., where the cutting element is an electrode). A computer associated with the controlling system checks electrical and fluidic viability of the device. During this self-checking, the computer can measure 2302 the electrical resistance of the electrode. If outside the allowed range for a good or fully functional/acceptable device, an alarm or other notification mechanism (e.g., lights, beeping, vibration, text displayed on screen, etc.) notifies 2304 user to replace it, and computer will not execute the surgical program until the problem is remedied. If the resistance is good and within the acceptable range, the operation may proceed. The computer continues to make resistance measurements 2302 at predetermined intervals (e.g., once per second). Similarly if any measurement indicates a problem, an alarm can alert 2304 the user and the procedure can be halted. Note that a unit that has previously been used in a surgical procedure will have a high resistance above the allowed range, so the computer prevents the accidental use of used or damaged units.

Also during the self-checking procedure, the computer can measure 2306 air flow rate versus pressure (i.e., clean dry filtered air can be blown out through the suction cup for this test). If not within the allowed range, an alarm or other notification system notifies 2308 the user to replace the device or otherwise correct the problem, and the computer will not execute the surgical program until it is corrected. This is done at least once at plug in, before the user has a chance to move on to any further steps. Once the preparatory steps are completed 2310, the device is ready for use.

Figure 24:
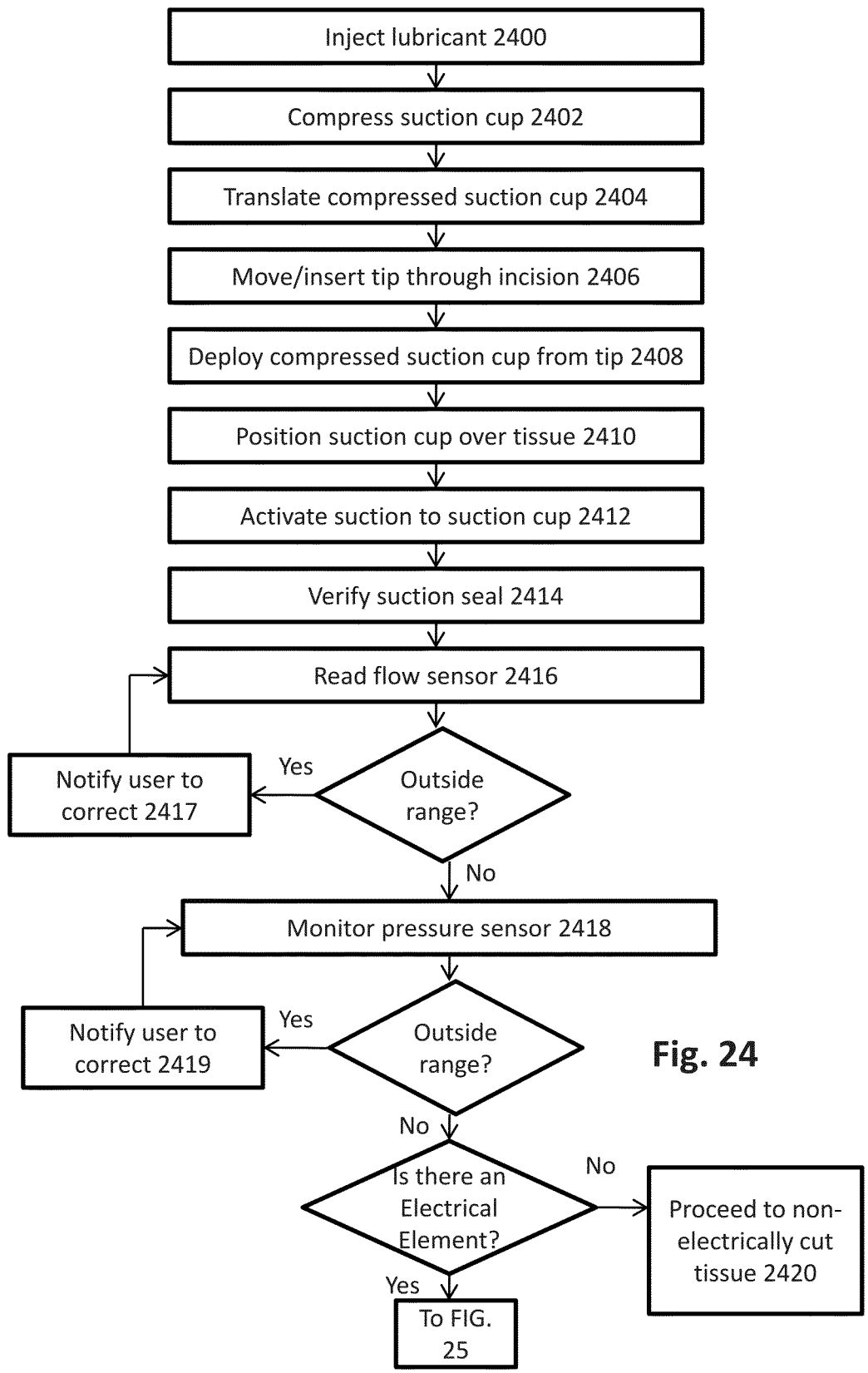
FIG. 24 is a flow chart illustrating steps for the microsurgery/capsulotomy procedure, according to an embodiment of the invention.

FIG. 24 is a flow chart illustrating steps for the microsurgery/capsulotomy procedure, according to an embodiment of the invention. The user can inject 2400 lubricant (e.g., viscoelastic) onto the suction cup for lubrication. Viscoelastic is commonly used in cataract surgery to keep the anterior chamber of the eye inflated. The user compresses 2402 the suction cup by manipulating the device (e.g., via the knob 8 or via the slidable ring 94). For device 1, the user performs step 2402 by pushing the knob 8 along slot 9 to translate the suction cup/compression mechanism ensemble up to the entrance of the insertion tip 3, which moves the compression arms distally to press the arms against internal walls of the handpiece 5, moving the arms inward toward each other to compress the suction cup 2. For device 90, the user performs step 2402 by sliding the slidable ring 94 distally over the compression arms 93, pressing the arms 93 together to compress the suction cup 99. The user can then further manipulate the device to translate 2404 the lubricated and compressed suction cup into the insertion tip of the device. For device 1, the user performs step 2404 by further pushing knob 8 along slot 9 to move the suction cup 2 distally into the tip 3. For device 90, the user performs step 2404 by pushing the piston 97 to move the suction cup 99 to the tip of the device.

The user moves/inserts 2406 the tip of the capsulotomy device through an incision in the tissue (e.g., the cornea of the eye). In some embodiments of the procedure, one or both of steps 2402 and 2404 occur before step 2406, so that the suction cup is compressed 2402 and/or translated 2404 into the insertion tip after insertion 2406 of the tip through the incision. The user deploys 2408 the compressed suction cup out through the tip of the handpiece to the tissue (e.g., into the anterior chamber to the lens capsule). The suction cup expands inside the tissue (e.g., into the anterior chamber of the eye, past the cornea) into a cutting position (e.g., on the lens capsule). For devices, such as device 1 and 90, the suction cup is mounted to a sliding element, so deploying the compressed suction cup includes translating the sliding element distally to move the suction cup within the handpiece, out through the tip and to the tissue. The user can then position 2410 the suction cup by centering it over the tissue, and orient pitch and roll to seat it against the tissue (e.g., the lens capsule). The user activates 2412 the suction to pull the suction cup against tissue, and thereby force the cutting element against the tissue (e.g., lens capsular membrane).

The user can verify 2414 that the desired low leakage suction seal has been established by moving the device horizontally or vertically (e.g., by 0.25 mm) to make sure that the lens moves with it. The user can further perform one or more system checks for the suction cup seal. The controlling computer can also verify that a low leakage seal has been established by reading 2416 the flow sensor that should show little or no liquid flow in the suction line. The pressure sensor is also monitored 2418, since a threshold low pressure will typically be reached in the suction line before the computer will proceed with the surgical program. If either the reading 2416 or the monitoring 2418 show a problem, the user can be notified, 2417, 2419 to correct the problem. The user then proceeds to the begin usage of the device for cutting of tissue with the cutting element. Where there is no electrical cutting element on the device, the user proceeds to non-electrically cut 2420 the tissue. For example, the user can cut 2420 the tissue via the suction applied to the suction cup to pull the tissue against the mechanical cutting element (e.g., sharp blade(s)). Where there is an electrical cutting element on the device, the procedure proceeds to FIG. 25 for electrical cutting steps.

Figure 25:
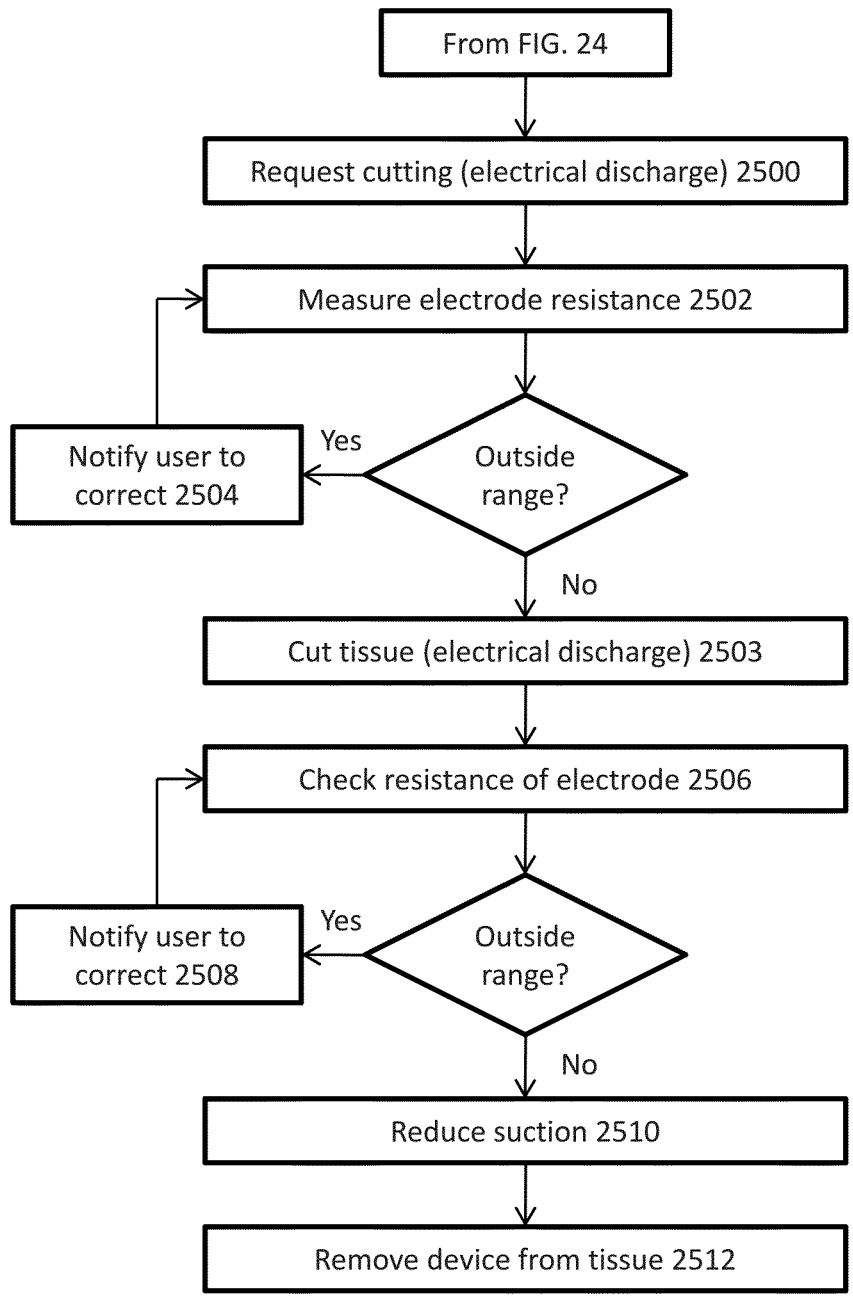
FIG. 25 is a flow chart illustrating a continuation of the steps for the microsurgery/capsulotomy procedure, according to an embodiment of the invention.

FIG. 25 is a flow chart illustrating a continuation of the steps for the microsurgery/capsulotomy procedure, according to an embodiment of the invention. The user requests 2500 the electrical discharge for cutting (e.g., via any type of user interface, such as by pressing a button, verbally with voice recognition software, etc.). The controlling computer does one last measurement 2502 of the electrode resistance, pressure and flow sensors. If all conditions are in range, the cutting occurs 2503 and the discharge is delivered. If not, the user is notified 2504 and can take action to remedy any problems. The electrical discharge for surgery may include several stages, such as the following: 1) degas (e.g., electrode held at 60° C. to 99° C.), 2) thermal tangling (e.g., electrode held at 60° C. to 99° C.), 3) cutting discharge (e.g., electrode heated to 200° C. to 1000° C.), and/or 4) electrode modifying spike (e.g., brief current spike to melt one or more electrode components). After discharge, the system checks 2506 the resistance of the electrode. If the resistance is outside the expected post-discharge range, an alarm notifies 2508 the user that an anomaly occurred and to execute appropriate diagnostic procedures. Otherwise, the user can proceed to the next step.

The user then reduces 2510 suction applied to the suction cup. The suction vacuum is reduced to allow the user to pull the suction cup away from the tissue. If the excised patch of membrane has been sucked into the lumen of the stem, then the suction can be completely turned off. Otherwise some suction can be maintained to the level needed to ensure that the patch is held and removed from the eye along with the device. The user then removes 2512 the device from the tissue (e.g., from the eye).

Device Fabrication

A variety of different mechanisms can be used in fabricating the components of the device. For example, the components of the handpiece can be made by injection molding of plastic. The suction cup can be made by overmolding a suitable elastomer (e.g., silicone, or polyurethane) over the electrode and stem, which have been positioned in the mold, though other materials can be used as well. The suction cup is designed to be collapsible to a small cross section so that it can be inserted through a corneal incision (e.g., an incision of less than 2 to 3 mm in length) but then can rapidly return to its circular shape after deployment. The thinner the walls are, the stiffer (higher durometer) the material can be. The size for the suction cup can range from about 4.5 mm to about 7 mm in diameter, while the height would commonly range from about 0.5 mm to about 1.5 mm. The suction cup and overall device design and size ranges can vary to match the surgical procedure being conducted.

The cutting element can be made from various materials. The metallic components of the electrode can be made by electroforming of suitable metals such as nickel, gold, steel, copper, platinum, iridium, etc. Connections between the electrode and leads in the stem can be made by electroplating, or welding. Typically, for electrical cutting elements, the material for the cutting element is electrically conductive, and for mechanical cutting elements, the material is hard enough to pierce the membrane. For both electrical and mechanical cutting elements, the material is also generally elastic enough to return to its prior shape after being squeezed to get through the tissue incision, or soft enough to be pushed back into circular shape by the polymeric support ring and/or by the suction cup in which it is mounted. For example, for an electrical cutting element, the materials can include those made by photochemical etching, such as spring steel, stainless steel, titanium nickel alloy, graphite, nitinol (NiTi alloy "memory metal"), nickel, nickel-chrome alloy, tungsten, molybdenum, or any other material that will allow the element to return to its prior shape. Other materials for electrical cutting elements include electrically conductive elastomers, including elastomers (e.g., silicone or polyurethane) mixed with appropriately shaped conductive particles (e.g., silver, gold, graphite, copper, etc) that can establish contact with each other and continue to be in contact with each other for the duration of the electrical discharge. An additional example of a material for electrical cutting elements includes a compliant mesh of very fine wires (e.g., diameter of about 1 or 2 microns) that can be anchored in the elastomeric support ring to make the conductive element. As a further example, materials can be used for electrical cutting elements that are made by sputtering metal onto a polymeric support, such as high conductivity metals (e.g., gold, aluminum, copper, etc.), which can be used to make very thin (e.g., 1 micron) elements with resistance within the usable range (e.g., 1 to 10 ohms) deposited by RF plasma sputtering.

Materials used for mechanical cutting elements can include photochemically etched metal (e.g., stainless steel), or a relatively hard plastic (e.g., phenolic), among others. Discrete micro teeth could be etched from single crystal silicon. Photochemical etching can used to make cutting elements that have a thickness of, for example, 25 microns, or 12.5 microns, or 5 microns, and so forth.

The above description is included to illustrate the operation of the embodiments and is not meant to limit the scope of the invention. The scope of the invention is to be limited only by the following claims. From the above discussion, many variations will be apparent to one skilled in the relevant art that would yet be encompassed by the spirit and scope of the invention. As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

What is claimed is:

1. A capsulotomy device for accessing a lens capsule through a cornea of an eye, the device comprising:
   a handpiece;
   a stem coupled to the handpiece, the stem including a conductive tube and an adjacent wire insulated from the conductive tube;
   a suction cup coupled to the stem, the conductive tube, and the adjacent wire, the suction cup including:
     an inner diameter wall, an outer diameter wall, and a roof, the inner diameter wall, the outer diameter wall, and the roof forming a channel,
     a ridge protruding from the roof such that the channel comprises two suction channels, and
     a lip protruding from an edge of the outer diameter wall, where the circumference of the lip increases in the radial direction away from the outer diameter wall, coupled to the outer diameter wall, the lip configured to be pulled against a capsular membrane of the eye to form a seal to allow pressure inside the channel to decrease; and
   a cutting element connected to the conductive tube and the adjacent wire,
   wherein the conductive tube and the adjacent wire are configured to deliver electrical energy to the cutting element for excising a portion of the lens capsule.

2. The capsulotomy device of claim 1, wherein the channel of the suction cup has a circular shape.

3. The capsulotomy device of claim 1, wherein the conductive tube is configured to apply suction to the suction cup to secure the suction cup against the lens capsule.

4. The capsulotomy device of claim 1, wherein the suction cup further comprises:
   one or more anchoring tabs, the anchoring tabs for securing the cutting element to the suction cup.

5. The capsulotomy device of claim 1, wherein the suction cup has a circular shape, and wherein the suction cup is collapsible to a cross section that can be inserted through a corneal incision of less than 3 mm in length.

6. The capsulotomy device of claim 1, wherein the stem is coupled to the suction cup through the outer diameter wall of the suction cup.

7. The capsulotomy device of claim 1, wherein suction is applied to the channel of the suction cup through the conductive tube.

8. The capsulotomy device of claim 1, further comprising:
   a compression device comprising at least one arm that is slidable relative to the handpiece for causing a change in shape of the suction cup; and
   a manipulation device connected through the handpiece to the compression device, the manipulation device configured to slide the compression device relative to the cutting element to cause the change in shape of the suction cup.

9. The capsulotomy device of claim 1, further comprising:
   a second lip protruding from an edge of the inner diameter wall, where the circumference of the lip decreases in the radial direction away from the inner diameter wall.

10. A device to be used during a capsulotomy, the device comprising:
    a stem including a conductive tube and an adjacent wire insulated from the conductive tube;
    a suction cup coupled to the stem, the conductive tube, and the adjacent wire, the suction cup including:
      an inner diameter wall, an outer diameter wall, and a roof, the inner diameter wall, the outer diameter wall, and the roof forming a channel,
      a ridge protruding from the roof such that the channel comprises two suction channels;
      a lip protruding from an edge of the outer diameter wall, where the circumference of the lip increases in the radial direction away from the outer diameter wall, coupled to the outer diameter wall, the lip configured to be pulled against a capsular membrane of an eye to form a seal to allow a pressure inside the channel to decrease; and
    a cutting element connected to the conductive tube and the adjacent wire, wherein the conductive tube and the adjacent wire are configured to deliver electrical energy to the cutting element for excising a portion of the lens capsule.

11. The capsulotomy device of claim 10, wherein the channel of the suction cup has a circular shape.

12. The capsulotomy device of claim 10, wherein the conductive tube is configured to apply suction to the suction cup to secure the suction cup against the capsular membrane.

13. The capsulotomy device of claim 10, wherein the suction cup has a circular shape, and wherein the suction cup is collapsible to a cross section that can be inserted through a corneal incision of less than 3 mm in length.

14. The capsulotomy device of claim 10, further comprising:
 a compression device comprising at least one arm that is slidable relative to a handpiece of the device for causing a change in shape of the suction cup; and
 a manipulation device connected through the handpiece to the compression device, the manipulation device configured to slide the compression device relative to the cutting element to cause the change in shape of the suction cup.

15. The capsulotomy device of claim 10, further comprising:
 a second lip protruding from an edge of the inner diameter wall, where the circumference of the lip decreases in the radial direction away from the inner diameter wall.

\* \* \* \* \*